(12) United States Patent
Rickus et al.

(10) Patent No.: US 11,919,941 B2
(45) Date of Patent: Mar. 5, 2024

(54) CELL-COLLAGEN-SILICA COMPOSITES AND METHODS OF MAKING AND USING THE SAME

(71) Applicant: Purdue Research Foundation, West Lafayette, IN (US)

(72) Inventors: Jenna Leigh Rickus, West Lafayette, IN (US); Sherry L. Voytik-Harbin, Zionsville, IN (US); Jennifer L. K. Rich, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 33 days.

(21) Appl. No.: 15/568,262

(22) PCT Filed: Apr. 21, 2016

(86) PCT No.: PCT/US2016/028686
§ 371 (c)(1),
(2) Date: Oct. 20, 2017

(87) PCT Pub. No.: WO2016/172365
PCT Pub. Date: Oct. 27, 2016

(65) Prior Publication Data
US 2018/0141996 A1   May 24, 2018

Related U.S. Application Data

(60) Provisional application No. 62/150,439, filed on Apr. 21, 2015.

(51) Int. Cl.
| | | |
|---|---|---|
| *C07K 14/78* | (2006.01) | |
| *C12N 5/00* | (2006.01) | |
| *C12N 5/071* | (2010.01) | |
| *C12N 11/04* | (2006.01) | |
| *C12N 11/14* | (2006.01) | |

(52) U.S. Cl.
CPC ............ *C07K 14/78* (2013.01); *C12N 5/0012* (2013.01); *C12N 5/0697* (2013.01); *C12N 11/04* (2013.01); *C12N 11/14* (2013.01)

(58) Field of Classification Search
CPC ..... A61K 2300/00; A61K 35/39; A61L 27/54; A61L 27/56; A61L 27/3633; A61L 27/38; A61L 15/60; A61L 2400/06; A61L 27/24; A61L 2300/622; A61L 2300/624; A61L 17/145; A61L 2300/606; C12N 2533/54; C12N 5/0012; C12N 5/0677; C12N 2513/00; C12N 5/0697; C12N 11/04; C12N 11/14; C08G 2210/00; C07K 14/78
See application file for complete search history.

(56) References Cited

U.S. PATENT DOCUMENTS

| | | |
|---|---|---|
| 3,949,073 A | 4/1976 | Daniels et al. |
| 4,233,360 A | 11/1980 | Luck et al. |
| 4,439,521 A | 3/1984 | Archer et al. |
| 4,544,516 A | 10/1985 | Hughes et al. |
| 4,582,640 A | 4/1986 | Smestad et al. |
| 4,600,533 A | 7/1986 | Chu et al. |
| 4,703,108 A | 10/1987 | Silver |
| 4,743,552 A | 5/1988 | Friedman et al. |
| 4,776,853 A | 10/1988 | Klement et al. |
| 4,789,663 A | 12/1988 | Wallace et al. |
| 4,801,299 A | 1/1989 | Brendel et al. |
| 4,829,000 A | 5/1989 | Kleinman et al. |
| 4,902,508 A | 2/1990 | Badylak et al. |
| 4,912,057 A | 3/1990 | Guirguis et al. |

(Continued)

FOREIGN PATENT DOCUMENTS

| | | |
|---|---|---|
| AU | 48841/99 | 3/2000 |
| CA | 2212704 | 8/1996 |

(Continued)

OTHER PUBLICATIONS

Foglia et al. A new method for the preparation of biocompatible silica coated-collagen hydrogels. J. Mater. Chem. B. 2013; 1:6283-6290.*
Stephens et al. Oligomeric collagen as an encapsulation material for islet/beta-cell replacement: effect of islet source, dose, implant site, and administration format. Am J Physiol Endocrinol Metab. 2020;319:E388-E400.*
Brasack et al. Biocompatibility of Modified Silica-Protein Composite Layers. Journal of Sol-Gel Science and Technology. 2000. 19:479-482.*
Xi et al. Pore size and pore-size distribution control of porous silica. Sensors and Actuators. 1995; B 24-25:347-352.*

(Continued)

*Primary Examiner* — Lynn Y Fan
(74) *Attorney, Agent, or Firm* — Barnes & Thornburg LLP

(57) ABSTRACT

Soluble, self-assembling collagens derived from tissues are extensively characterized such that one can predict and customize the final collagen-fibril matrix with respect to fibril microstructure (i.e., fibril density, interfibril branching), viscoelasticity and proteolytic degradability. As shown herein these matrices template and direct the deposition of mesoporous silica at the level of individual collagen fibrils. The fibril density, silicic acid concentration, and time of exposure to silicifying solution were varied and the resulting hybrid materials were analyzed by scanning electron microscopy, energy-dispersive x-ray spectroscopy, and rheology. Microstructural properties of the collagen-fibril template are preserved in the silica surface of hybrid materials. Results for three different collagen fibril densities, corresponding to shear storage moduli of 200 Pa, 1000 Pa, and 1600 Pa, indicate that increased fibril density increases the absolute amount of templated silica when all other silica synthesis conditions are kept constant. The mechanical properties of the hybrid material are dominated by the presence of the silica coating rather than the starting collagen matrix stiffness.

28 Claims, 10 Drawing Sheets

(56) References Cited

U.S. PATENT DOCUMENTS

| | | |
|---|---|---|
| 4,956,178 A | 9/1990 | Badylak et al. |
| 5,032,508 A | 7/1991 | Naughton et al. |
| 5,163,955 A | 11/1992 | Love et al. |
| 5,204,382 A | 4/1993 | Wallace et al. |
| 5,266,480 A | 11/1993 | Naughton et al. |
| 5,275,826 A | 1/1994 | Badylak et al. |
| 5,281,422 A | 1/1994 | Badylak et al. |
| 5,336,616 A | 8/1994 | Livesey et al. |
| 5,352,463 A | 10/1994 | Badylak et al. |
| 5,372,821 A | 12/1994 | Badylak et al. |
| 5,420,248 A | 5/1995 | Devictor et al. |
| 5,460,962 A | 10/1995 | Kemp et al. |
| 5,478,739 A | 12/1995 | Sivka et al. |
| 5,518,915 A | 5/1996 | Naughton et al. |
| 5,554,389 A | 9/1996 | Badylak et al. |
| 5,604,106 A | 2/1997 | Liotta et al. |
| 5,641,518 A | 6/1997 | Badylak et al. |
| 5,695,998 A | 12/1997 | Demeter et al. |
| 5,753,267 A | 5/1998 | Badylak et al. |
| 5,863,531 A | 1/1999 | Naughton et al. |
| 5,866,414 A | 2/1999 | Badylak et al. |
| 5,885,619 A | 3/1999 | Patel et al. |
| 5,948,429 A | 9/1999 | Bell et al. |
| 5,955,110 A | 9/1999 | Patel et al. |
| 6,020,200 A * | 2/2000 | Enevold .......... A61K 9/1652 264/4.3 |
| 6,022,743 A | 2/2000 | Naughton et al. |
| 6,087,157 A | 7/2000 | Badylak et al. |
| 6,099,567 A | 8/2000 | Badylak et al. |
| 6,171,344 B1 | 1/2001 | Atala |
| 6,187,039 B1 | 2/2001 | Hiles et al. |
| 6,187,047 B1 | 2/2001 | Kwan et al. |
| 6,206,931 B1 | 3/2001 | Cook et al. |
| 6,241,981 B1 | 6/2001 | Cobb et al. |
| 6,248,587 B1 | 6/2001 | Rodgers et al. |
| 6,264,992 B1 | 7/2001 | Voytik-Harbin et al. |
| 6,358,284 B1 | 3/2002 | Fearnot et al. |
| 6,375,989 B1 | 4/2002 | Badylak et al. |
| 6,379,710 B1 | 4/2002 | Badylak |
| 6,384,196 B1 | 5/2002 | Weis et al. |
| 6,419,920 B1 | 7/2002 | Mineau-Hanschke |
| 6,444,229 B2 | 9/2002 | Voytik-Harbin et al. |
| 6,475,232 B1 | 11/2002 | Babbs et al. |
| 6,485,723 B1 | 11/2002 | Badylak et al. |
| 6,497,875 B1 | 12/2002 | Sorrell et al. |
| 6,576,265 B1 | 6/2003 | Spievack |
| 6,586,493 B1 | 7/2003 | Massia et al. |
| 6,592,623 B1 | 7/2003 | Bowlin et al. |
| 6,592,794 B1 | 7/2003 | Bachrach |
| 6,666,892 B2 | 12/2003 | Hiles et al. |
| 6,682,670 B2 | 1/2004 | Noff |
| 6,793,939 B2 | 9/2004 | Badylak |
| 6,893,812 B2 | 5/2005 | Woltering et al. |
| 6,918,396 B1 | 7/2005 | Badylak et al. |
| 6,962,814 B2 | 11/2005 | Mitchell et al. |
| 7,029,689 B2 | 4/2006 | Berglund et al. |
| 7,087,089 B2 | 8/2006 | Patel et al. |
| 7,175,841 B2 | 2/2007 | Badylak et al. |
| 7,338,517 B2 | 3/2008 | Yost et al. |
| 7,771,717 B2 | 8/2010 | Badylak et al. |
| 7,795,022 B2 | 9/2010 | Badylak |
| 7,815,686 B2 | 10/2010 | Badylak |
| 8,084,055 B2 | 12/2011 | Voytik-Harbin et al. |
| 8,222,031 B2 | 7/2012 | Noll |
| 8,241,905 B2 | 8/2012 | Forgacs et al. |
| 8,343,758 B2 | 1/2013 | Cheema et al. |
| 8,431,158 B2 | 4/2013 | Shoseyov |
| 8,449,902 B2 | 5/2013 | Brown et al. |
| 8,512,756 B2 | 8/2013 | Voytik-Harbin et al. |
| 8,518,436 B2 | 8/2013 | Voytik-Harbin et al. |
| 8,580,564 B2 | 11/2013 | Brown et al. |
| 8,652,500 B2 | 2/2014 | Bosley, Jr. |
| 8,741,352 B2 | 6/2014 | Hodde et al. |
| 8,785,389 B2 | 7/2014 | Brown et al. |
| 9,101,693 B2 | 8/2015 | Brown et al. |
| 9,205,403 B2 | 12/2015 | Dubois |
| 9,707,703 B2 | 7/2017 | Tully |
| 9,744,123 B2 | 8/2017 | Castiglione-Dodd et al. |
| 9,757,495 B2 | 9/2017 | Murray |
| 10,314,940 B2 | 6/2019 | Voytik-Harbin |
| 2002/0076816 A1 | 6/2002 | Dai et al. |
| 2002/0170120 A1 | 11/2002 | Eckmayer et al. |
| 2002/0172705 A1 | 11/2002 | Murphy et al. |
| 2003/0113302 A1 | 6/2003 | Revazoa et al. |
| 2003/0216811 A1 | 11/2003 | Badylak |
| 2003/0216812 A1 | 11/2003 | Badylak |
| 2004/0006395 A1 | 1/2004 | Badylak |
| 2004/0030404 A1 | 2/2004 | Noll et al. |
| 2004/0037813 A1 | 2/2004 | Simpson et al. |
| 2004/0078076 A1 | 4/2004 | Badylak et al. |
| 2004/0137616 A1 | 7/2004 | Isseroff et al. |
| 2005/0014181 A1 | 1/2005 | Galis et al. |
| 2005/0019419 A1 | 1/2005 | Badylak et al. |
| 2005/0153442 A1 | 7/2005 | Katz et al. |
| 2005/0202058 A1 | 9/2005 | Hiles |
| 2005/0226856 A1 | 10/2005 | Ahlfors |
| 2005/0260748 A1 | 11/2005 | Chang et al. |
| 2005/0266556 A1 | 12/2005 | Yoder et al. |
| 2006/0014284 A1 | 1/2006 | Graeve |
| 2006/0134072 A1 | 6/2006 | Pedrozo et al. |
| 2006/0147501 A1 | 7/2006 | Hillas et al. |
| 2006/0165667 A1 | 7/2006 | Laughlin et al. |
| 2006/0235511 A1 | 10/2006 | Osborne |
| 2006/0257377 A1 | 11/2006 | Atala et al. |
| 2007/0026518 A1 | 2/2007 | Healy et al. |
| 2007/0077652 A1 | 4/2007 | Peled et al. |
| 2007/0141037 A1 | 6/2007 | Badylak et al. |
| 2007/0190646 A1 | 8/2007 | Engler et al. |
| 2007/0269476 A1 | 11/2007 | Voytik-Harbin et al. |
| 2008/0025956 A1 | 1/2008 | Yoder et al. |
| 2008/0070304 A1 | 3/2008 | Forgacs et al. |
| 2008/0095815 A1 | 4/2008 | Mao |
| 2008/0107750 A1 | 5/2008 | Hodde et al. |
| 2008/0181935 A1 | 7/2008 | Bhatia et al. |
| 2008/0199441 A1 | 8/2008 | Peled |
| 2008/0268052 A1 | 10/2008 | Voytik-Harbin et al. |
| 2009/0011021 A1 | 1/2009 | Voytik-Harbin et al. |
| 2009/0069893 A1 | 3/2009 | Paukshto et al. |
| 2009/0175922 A1 | 7/2009 | Voytik-Harbin et al. |
| 2009/0269386 A1 | 10/2009 | Zubery et al. |
| 2009/0280180 A1 | 11/2009 | Voytik-Harbin et al. |
| 2009/0324681 A1 | 12/2009 | Badylak |
| 2010/0119578 A1 | 5/2010 | To et al. |
| 2010/0143476 A1 | 6/2010 | March et al. |
| 2010/0272697 A1 | 10/2010 | Naji et al. |
| 2011/0182962 A1 | 7/2011 | McKay |
| 2011/0237552 A1 | 9/2011 | Heinemann et al. |
| 2012/0027732 A1 | 2/2012 | Voytik-Harbin et al. |
| 2012/0094376 A1 | 4/2012 | Voytik-Harbin et al. |
| 2012/0115222 A1* | 5/2012 | Voytik-Harbin ..... C12N 5/0647 435/375 |
| 2012/0141417 A1 | 5/2012 | Voytik-Harbin et al. |
| 2012/0171768 A1 | 7/2012 | Voytik-Harbin et al. |
| 2012/0189588 A1 | 7/2012 | Nahas et al. |
| 2012/0273993 A1 | 11/2012 | Shoseyov |
| 2012/0297550 A1 | 11/2012 | Ngo et al. |
| 2014/0051144 A1 | 2/2014 | Wackett et al. |
| 2014/0056865 A1 | 2/2014 | Samaniego et al. |
| 2014/0193473 A1 | 7/2014 | Yoder et al. |
| 2014/0193477 A1 | 7/2014 | Chaikof et al. |
| 2015/0105323 A1 | 4/2015 | Novak et al. |
| 2016/0175482 A1 | 6/2016 | Quirk et al. |
| 2018/0050130 A1 | 2/2018 | Jiang et al. |
| 2019/0351097 A1 | 11/2019 | Voytik-Harbin |

FOREIGN PATENT DOCUMENTS

| | | |
|---|---|---|
| DE | 201 15 753 U1 | 1/2002 |
| EP | 0443094 | 8/1991 |
| EP | 1264878 | 12/2002 |
| EP | 1 270 672 A1 | 1/2003 |
| EP | 1 674 116 A2 | 6/2006 |
| GB | 2366736 | 3/2002 |
| JP | 01-247082 | 10/1989 |

(56) References Cited

FOREIGN PATENT DOCUMENTS

| | | |
|---|---|---|
| JP | 6-510927 | 8/1994 |
| JP | 07 074239 B | 8/1995 |
| WO | 92/15676 | 9/1992 |
| WO | 93/00441 | 1/1993 |
| WO | 93/05798 | 4/1993 |
| WO | WO 94/03119 | 2/1994 |
| WO | 94/11008 | 5/1994 |
| WO | 94/23016 | 10/1994 |
| WO | 96/24661 | 8/1996 |
| WO | 97/17038 | 5/1997 |
| WO | 98/06445 | 2/1998 |
| WO | 98/25637 | 6/1998 |
| WO | 98/52637 | 11/1998 |
| WO | 00/15765 | 3/2000 |
| WO | 00/62833 | 10/2000 |
| WO | 01/10355 | 2/2001 |
| WO | WO 2001/023529 | 4/2001 |
| WO | 01/45765 | 6/2001 |
| WO | WO 2001/045765 | 6/2001 |
| WO | 01/48153 | 7/2001 |
| WO | 01/78754 | 10/2001 |
| WO | 02/07646 | 1/2002 |
| WO | 02/14480 | 2/2002 |
| WO | 02/20729 | 3/2002 |
| WO | 2002/102237 | 12/2002 |
| WO | 2003/068287 | 8/2003 |
| WO | 2003/071991 | 9/2003 |
| WO | 03/087337 | 10/2003 |
| WO | 03/092471 | 11/2003 |
| WO | 03/097694 | 11/2003 |
| WO | WO 04/028404 | 4/2004 |
| WO | 2004/060426 | 7/2004 |
| WO | WO 04/078120 | 9/2004 |
| WO | 2006/003442 | 1/2006 |
| WO | 2006/124946 | 11/2006 |
| WO | WO 2006/125025 | 11/2006 |
| WO | WO 2007/028079 | 3/2007 |
| WO | WO 2007/136634 | 11/2007 |
| WO | WO 2008/036393 | 3/2008 |
| WO | 00/47219 | 8/2008 |
| WO | 2008/124169 | 10/2008 |
| WO | WO 2009/076441 | 6/2009 |
| WO | WO 2010/123928 | 10/2010 |
| WO | WO 2011/009054 | 1/2011 |
| WO | 2012/004564 | 1/2012 |
| WO | 2017/044847 | 3/2017 |
| WO | 2018/144496 | 8/2018 |
| WO | WO 2019/023266 A1 | 1/2019 |

OTHER PUBLICATIONS

Siegel RC. Collagen Cross-linking Synthesis of Collagen Cross-Links in Vitro With Highly Purified Lysyl Oxidase.The Journal of Biological Chemistry. 1976;251(18):5786-5792.*
Krasucka et al. Effect of condensing tetraethoxysilane on desorption of organic compound from porous polymer. Adsorption Science & Technology. 2017;35(5-6):490-498.*
International Search Report and Written Opinion issued by the ISA/US, Commissioner for Patents, dated Jul. 12, 2016, for International Application No. PCT/US2016/028686; 8 pages.
Designation: F3089—14, Standard Guide for Characterization and Standardization of Polymerizable Collagen-Based Products and Associated Collagen-Cell Interactions, Jul. 2014, ASTM International.
Kreger et al., Polymerization and Matrix Physical Properties as Important Design Considerations for Soluble Collagen Formulations, Mar. 16, 2010, Biopolymers, 93 (8) 690-707.
"Basement Membrane" accessed online at http://en.wilipedia.org/wiki/Basement_membrane#Composition on Jun. 11, 2010.
"Extracellular Matrix" accessed at http://en.wikipedia.org/wiki/Extracellular_matrix on Jun. 11, 2010.
Bell, Brett J. et al., "Cell Density and Extracellular Matrix (ECM) Microstructure Control Mechanical Behavior of Engineered Tissue Constructs", *2005 Summer Bioengineering conference*, (Jun. 22-26, 2005).
Bjornsson, S., "Simultanelous Preparation and Quantitation of Proteoglycans by Precipitation with Alcian Blue", Analytical Biochemistry, vol. 210, 1993, pp. 282-291.
Brennan and Davison, "Role of aldehydes in collagen fibrillogenesis in vitro," Biopolymer, vol. 19, 1980, Issue 10, p. 1861-1873.
Brightman et al., "Time-Lapse Confocal Reflection Microscopy of Collagen Fibrillogenesis and Extracellular Matrix Assembly In Vitro", *Biopolymers*, vol. 54, 222-234, (2000).
Callister, W. D, Jr., Materials Science and Engineering: an Introduction, $3^{rd}$ edition, New York, NY, John Wiley & Sons, Inc., 1994.
Chandrakasan et al. J. Biol. Chem., 1976, 251:6062-67.
Ciovacco et al., Bone, 2009, 44(1):80-86.
Comper, W. E., and A. Veis, "Characterization of Nuclei in in Vitro Collagen Fibril Formation", Biopolymer, vol. 16, 1977, pp. 2133-2142.
Compston, "Bone marrow and bone: a functional unit," Journal of Endocrinology, 173: 387-394, 2002.
Davis, et al., "Injectable Self-Assembling Peptide Nanofibers Create Intramyocardial Microenvironments for Endothelial Cell", *Circulation*, 111, 442-50, (Feb. 1, 2005).
Fulzele, S. V., P. M. Satturwar, A. K. Dorle, "Study of the Biodegradation and in Vivo Biocompatibility of Novel Biomaterials", European Journal of Pharmaceutical Sciences, vol. 20, 2003, pp. 53-61.
Gallop, P. M., and S. Seifter, "Preparation and Properties of Soluble Collagens", Soluble Collagens, 1963, pp. 635-641.
Gelman et al., "Collagen Fibril Formation in Vitro," J. Biol. Chem., 1979, 254(22): 11741-11745.
Gelman et al., "Collagen Fibril Formation," J. Biol. Chem., 1979, 254(1):180-186.
Griffey, S., N. D. Schwade, C. G. Wright, "Particulate Dermal Matrix as an Injectable Soft Tissue Replacement Material", J. Biomed. Mater. Res. vol. 58, 2001, pp. 10-15.
Hou, et al., "Radiolabeled Cell Distribution After Intramyocardial, Intracoronary, and Interstitial Retrograde Coronary Venous Delivery", *Circulation*, 112, 150-6, (Aug. 30, 2005).
Hunt, T. K., P. Twomey, B. Zederfeldt, and J. E. Dunphy, "Respiratory Gas Tensions and PH In Healing Wounds", American Journal of Surgery, vol. 114, 1967, pp. 302-307.
Ingram, D. A., et al., "Identification of a Novel Hierarchy of Endothelial Progenitor Cells Using Human Peripheral and Umbilical Cord Blood", Blood, 104, 2752-2760, (2004).
International Search Report and Written Opinion for PCT/US2006/018998 filed May 16, 2006.
International Search Report and Written Opinion dated Nov. 29, 2007 for PCT/US2006/019130.
International Search Report for International Application No. PCT/US07/020463, dated Feb. 21, 2008, 6 pgs.
International Search Report/Written Opinion for PCT/US2007/011681 completed Nov. 6, 2007.
Kacena et al., J. of Histotechnology, 2004, 27:119-130.
Knott et al., "Collagen Cross-Links in Mineralizing Tissues: A Review of Their Chemistry, Function, and Clinical Relevance," 1998, 22(3):181-187.
Kondo et al., "Biology of Hematopoietic Stem Cells and Progenitors: Implications for Clinical Application," Annu. Rev. Immunol., 2003, 21:759-806.
Korff et al., Jour. of Cell Science, vol. 112: 3249-3258 (1999).
Kreger et al., "Hyaluronan concentration within a 3D collagen matrix modulates matrix visoelasticity, but not fibroblast response," Matrix Biol., 2009, 28(6):336-46.
Kreger, "Design of 3D Collagen Matrices for Cell Delivery and Guidance in Tissue Engineering," Thesis Submitted to the Faculty of Purdue University in Partial Fulfillment of the Requirements for the Degree of Doctor of Philosophy, May 2009, Purdue University.
Lin et al., "Comparison of Physical-Chemistry Properties of Type I Collagen from Different Species," *Food Chemistry*. 99(2): 244-251 (2005).
Malvern, *Introduction to the Mechanics of a Continuous Medium*. Upper Saddle River, NJ: Prentice-Hall, 1969.

(56) References Cited

OTHER PUBLICATIONS

Marotta, M., G. Martino, "Sensitive Spectrophotometric Method for the Quantitative Estimation of Collagen", Analytical Biochemistry, vol. 150, 1985, pp. 86-90.
Miller et al., "Preparation and Characterization of the Different Types of Collagen," Methods in Enzymology, 82: 33-64 (1982).
Miller, E. J., E. H. Epstein, Jr., and K. A. Piez, "Identification of Three Genetically Distinct Collagens by Cyanogen Bromide Cleavage of Insoluble Human Skin and Cartilage Collagen", Biochemical and Biophysical Research Communications, vol. 42, No. 6, 1971, pp. 1024-1029.
Na, "Monomer and Oligomer of Type I Collagen: Molecular Properties and Fibril Assembly," Biochemistry, 1989, 28(18):7161-7167.
Narmoneva et al., "Endothelial Cells Promote Cardiac Myocyte Survival and Spatial Reorganization", Circulation, 110, 962-968, (Aug. 24, 2004).
Nguyen et al., "Comparison of the Amino Acid Composition of Two Commercial Porcine Skins (Rind),"Journal of Agricultural and Food Chemistry, 34(3): 565-572 (1986).
Nielsen, T. B. and J. A. Reynolds, "Measurements of Molecular Weights by Gel Electrophoresis", Methods in Enzymology, vol. 48, Hirs and Temasheff, Eds., Academic Press, New York, 1978, pp. 3-10.
Orschell-Traycoff et al., Blood, 2000, 96:1380-1387.
Osborne, et al., "Investigation into the tensile properties of collagen/chondroitin-6-sulphate gels: the effect of crosslinking agents and diamines", Medical & Biological Engineering & Computing, vol. 36, 129-134, (1998).
Ozerdem, et al., "Physical Response of Collagen Gels to Tensile Strain", Journal of Biomechanical Engineering, vol. 117, 397-401, (Nov. 1995).
Pizzo et al., "Cell-Extracellular Matrix (ECM) Micro-Mechanical Behavior Depends on ECM Microstructure and Cell Type", 2005 Summer Bioengineering Conference, (Jun. 22-26, 2005).
Pizzo et al., "Extracellular matrix (ECM) microstructural composition regulates local cell-ECM biomechanics and fundamental fibroblast behaviour: a multidimensional perspective", J Appl PHysiol, 98: 1909-1921, (2005).
Pizzo et al., "Long-term Production of Choline Acetylatransferase in the CNS After Transplantation of Fibroblasts Modified with a Regulatable Vector", Mol Brain Res, 126, 1-13 (2004).
Rehman, et al., "Secretion of Angiogenic and Antiapoptotic Factors by Human Adipose Stromal Cells", Circulation. 109: 1292-8, (Mar. 16, 2004).
Reinlib, et al., "Cell Transplantation as Future Therapy for Cardiovascular Disease!", Circulation, 101: e182-e187.
Roeder B. A., K. Kokini, J. E. Sturgis, J. P. Robinson, S. L. Voytik-Harbin, "Tensile Mechanical Properties of Three-Dimensional Type 1 Collagen Extrancellular Matrices with Varied Microstructure", J. Biomech. Eng., vol. 124, 2002. pp. 214-222.
Roeder et al., "Local, Three-Dimensional Strain Measurements Within Largely Deformed Extracellular Matrix Constructs", J Biomech Eng, 126, 699-708, (2004).
Scadden, "The stem cell niche as an entity of action," Nature, 441; 1075-1079, 2006.
Schechner et al., "In vivo formation of complex microvessels lined by human endothelial cells in an immunodeficient mouse," PNAS, Aug. 1, 2000, vol. 97, No. 16, 9191-9196.
Schilling, J. A., W. Joel, H. M. Shurley, "Wound Healing: A Comparative Study of the Histochemical Changes in Granulation Tissue Contained in Stainless Steel Wire Mesh and Polyvinyl Sponge Cylinder", Surgery, vol. 46, No. 4, Oct. 1959, pp. 702-710.
Shiozawa et al., "The bone marrow niche: habitat to hematopoietic and mesenchymal stem cells, and unwitting host to molecular parasites," Leukemia, 22(5): 941-950, 2008.
Sieminski et al., Expt. Cell Res., vol. 297, pp. 574-584 (2004).
Spradling et al., "Stem Cells Find Their Niche," Nature, 414: 98-104, 2001.
Strang, et al., Linear Algebra and Its Applications. 3rd edition. San Diego, CA: Academic Press, 1988.
Sykes, B., B. Puddle, M. Francis, and R. Smith, "The Estimation of Two Collagens from Human Dermis by Interrupted Gel Electrophoresis", Biochemical and Biophysial Research Communications, vol. 72, No. 4, 1976, pp. 1472-1480.
Veis, Arthur, et al., "Fundamentals of Interstitial; Collagen Self-Assembly", 1994, Extracellular Matrix Assembly and Structure, Academica Press, pp. 15-45.
Voytik-Harbin et al., "Application and Evaluation of the Alamarblue Assay for Cell Growth and Survival of Fibroblasts", In Vitro Cell Dev Biol Anim, 34, 239-246, (1998).
Voytik-Harbin et al., "Simultaneous Mechanical Loading and Confocal Reflection Microscopy for Three-Dimensional Microbiomechanical Analysis of Biomaterials and Tissue Constructs", Microsc Microanal, 9, 74-85, (2003).
Voytik-Harbin et al., Small Intestinal Submucosa: A Tissue-Derived Extracellular Matrix That Promotes Tissue-Specific Growth and Differentiation of Cells in Vitro, Tissue Engineering4, 2, 157-174, (1998).
Voytik-Harbin et al., "Three-Simensional Imaging of Extracellular Matrix and Extracellular Matrix-Cell Interactions", Methods in Cell Biology, 63, 583-597, (2001).
Wess, Collagen fibrillar structure and hierarchies in P. Fratzl (ed.), Collagen: Structure and Mechanics, Springer Science + Business Media, LLC, New York, 2008, 53-60.
Yoder et al., "Redefining endothelial progenitor cells via clonal analysis and hematopoietic stem/progenitor cell principals," BLOOD, 2007, 109:1801-1809.
International Search Report and Written Opinion for PCT/US2008/086232, dated Jan. 16, 2009, 12 pages.
Bailey JL et al., "Collagen Oligomers Modulate Physical and Biolocial Properties of Three-Dimensional Self-Assembled Matrices," Biopolymers, 2010; 95(2): 77-93.
Na et al., "In Vitro Collagen Fibril Assembly in Glycerol Solution: Evidence for a Helical Cooperative Medhanism Involving Microfibrils," Biochemistry, 1986; 25: 958-966.
Na et al., "Mechanism of in Vitro Collagen Fibril Assembly," Journal of Biological Chemistry, 1986; 261(26): 12290-12299.
Voytik-Harbin et al., "Identification of Extractable Growth Factors from Small Intestine Submucosa," J Cell. Biochemistry, 1997; 67: 478-491.
Condell RA et al., "Analysis of Native Collagen Monomers and Oligomers by Size-Exclusion High-Performance Liquid Chromatography and its Applications," Analytical Biochemistry, 1993; 212: 436-445.
"Density" from Merriam-Webster online, accessed on Feb. 1, 2011.
Brandner et al., "replicating the Hematopoietic Stem Cell Niche," Purdue University, BME Graduate Student Association Research Symposium, Poster Presentation, Jul. 16, 2009.
Whittington et al., "Collagen oligomers modulate physical and cell-instructive properties of polymerizable collagen matrices," Biomaterials Day Society fo Biomaterials, Nov. 6, 2010 (PowerPoint presentation and poster).
Kreger et al., "Polymerization and matrix physical properties as important design considerations for soluble collagen formulations," 2010, Biopolymers, 93(8): 690-707.
Critser et al., "Collagen matrix physical properties modulate endothelial colony forming cell-derived vessels in vivo," 2010, Microvasc. Res., 80(1): 23-30.
Munakata, et al., Glycobiology, vol. 9, 1023-1027 (1999).
Kim, "Characterization of Acid-soluble Collagen from Pacific Whiting Surimi Processing Byproducts," J. Food Science. 2004, 69: C637-C642.
Billiar, Cellular and Biomolecular Mechanics and Mechanobiology, Amit Gefen, Ed., p. 210 (2011).
Ho et al., "Characterization of Collagen Isolation and Application of Collagen Gel as a Drug Carrier", J. of Controlled Release, vol. 44, pp. 103-112 (1997).
Liu, Asian-Aust J. Anim. Sci, 2001; 14(11):1638-1644.
Lynn et al., "Antigenicity and immunogenicity of collagen," J Biomed Mater Res, Part B: Appl Biomater, 2004; 71B:343-354.
Taichman et al., "Human Osteoblasts Support Hematopoiesis through the Production of Granulocyte Colony-stimulating Factor," Journal of Experimental Medicine, 1994; 179:1677-1682.

(56) References Cited

OTHER PUBLICATIONS

TeBmar et al., "Hydrogels for tissue engineering," *Fundamentals of Tissue Engineering and Regenerative Medicine*. 2009; p. 495-517.
Koken, "About Collage," Technical information, Support webpage, 2006.
Taqvi et al., "Influence of scaffold physical properties and stromal cell coculture on hematopoietic differentiation of mouse embryonic stem cells," *Biomaterials*, 2006; 24:6024-6031.
Engler et al., "Matrix elasticity directs stem cell lineage specification," *Cell*, 2006; 126:677-689.
Young, et al., "Adult Stem Cells." Anat. Record Pt. A: Disc. Mol. Cell. Evol. Biol. 276A:75-102 (2004).
Yang, et al., "The application of recombinant human collagen in tissue engineering." *Biodrugs* 18:103-119 (2004).
Fischbach, et al., "Three-dimensional in vitro model of adipogenesis: coparison of culture conditions." *Tissue Engineering* 10:215-229 (2004).
Reinisch et al, "Humanized large-scale expanded endothelial colony-forming cells function in vitro and in vivo." *Blood*, 2009; 113:6716-6725.
Silver et al., "Collagen self-assembly and the development of tendon mechanical properties," *Journal of Biomechanics*, 2003; 36:1529-1553.
Product information: Collagen Solution—Type 1 from rat tail, Sigma, http://www.sigmaaldrich.com/etc/medialib/docs/Sigma/Datasheet/3/c3867dat.Par.0001.File.tmp/c3867dat.pdf.
Gallagher D, "Stem cells being made from blood," available at www.bbc.co.uk/news/health-20539835.
Ingram D et al., "Vessel wall-derived endothelial cells rapidly proliferate because they contain a complete hierarchy of endothelial progenitor cells," *Blood*, 2005; 105(7):2783-6 (Epub Dec. 7, 2004).
Ingram D et al., "Unresolved questions, changing definitions, and novel paradigms for defining endothelial progenitor cells via clonal analysis and hematopoietic stem/progenitor cell principals," *Blood*, 2007; 109(5):1801-9 (Epub Oct. 19, 2006).
Prater DN et al., "Working hypothesis to redefine endothelial progenitor cells," *Leukemia*, 2007; 21(6):1141-9 (Epub Mar. 29, 2007).
Case J et al., "Human CD34+AC133+VEGFR-2+ cells are not endothelial progenitor cells but distinct, primitive hematopoietic progenitors," *Exp Hematol.*, 2007; 35(7):1109-18.
Hirschi KK et al, "Assessing identify, phenotype, and fate of endothelial progenitor cells," *Arterioscler Thromb Vasc Biol*, 2008; 28(9):1584-95 (Epub Jul. 31, 2008).
Timmermans F et al., "Endothelial progenitor cells: identify defined?", *J Cell Mol Med*, 2009; 13(1):87-102.
Mund JA et al, "Endothelial progenitor cells and cardiovascular cell-based therapies," *Cytotherapy*, 2009; 11(2):103-13.
Chor Wing Tam et al. EWMA Journal, 2012; 12(2).
Boyd et al. Atlas and Text of Corneal Pathology and Surgery; 2011 [Document REJECTED by EXAM. because illegible].
Stem Cell Differentiation (science and global issues/biology, cell biology), 2013.
Shimizu, "Fabrication of pulsatile cardiac tissue grafts using a novel 3-dimensional cell sheet manipulation technique and temperature-responsive cell culture surfaces," Circ Res., 2002, 90:e40-48.
Mizuno et al., "Osteogenesis by bone marrow stromal cells maintained on type 1 collagen matrix gels in vivo." Bone 20:101-107 (1997).
Young et al., "Use of meschymal stem cells in a collagen matrix for Achilles tendon repair." J. Orthopaedic Res. 16 406-413 (1998).
Vasiliev and Gelfand, Neoplastic and Normal Cells in Culture, Cambring University Press, p. 19, 1981.
"Stem Cells and the future of Regenerative Medicine" published by National Academy of Sciences, p. 19, 2002.
McBeath et al., "Cell shape, cytoskeletal tension, and RhoA regulate stem cell lineage commitment," *Developmental Cell*, 2004; 6:483-495.
Engler et al., "Myotubes differentiate optimally on substrates with tissue-like stiffness: pathological implications for soft or stiff microenvironments," *Journal of Cell Biology*, 2004; 165:877-887.
Kong et al., "FRET measurements of cell-traction forces and nano-scale clustering of adhesion ligands varied by substrate stiffness," *PNAS*, 2005; 102:4300-4305.
Settleman, "Tension Precedes Commitment—Even for a Stem Cell," *Molecular Cell*, 2004; 14:148-150.
Engler et al., "Substrate elasticity directs adult mesenchymal stem cell differentiation," Abstract 783, The 37th Middle Atlantic Regional Meeting, May 2005.
Wang et al, Sheng Li Xue Bao, 2005, 57(2): 259-269; Astract Only.
Williams et al, 1978, Journ Biol Chem, 253: 6578-6585.
Huang et al, 2005, Mechanisms and Dynamics of Mechanical Strengthening in Ligament-Equivalent Fibroblast-Populated Collagen Matrices, Annals of Biomedical Engineering, 21: 289-305.
Rucha Joshi: "Purdue e-Pubs Open Access Dissertations Theses and Dissertations Designer Collagen-Fibril Biograft Materials for Tunable Molecular Delivery," Jan. 1, 2016 https://docs.lib.purdue.edu/open_access_dissertations/1218.
"Artificial Blood Vessel," English translation of Japanese Patent Application Publication No. 3-12169, 1991, 16 pages.
Asem, E.K. et al. "Basal lamina of Avian Ovarian Follicle: Influence on Morphology of Granulosa Cells In-Vitro," Comparative Biochemistry and Physiology, Part C, 125 (2000), pp. 189-201.
Boder G.B. et al. "Long-Term Production of Insulin by Isolated Rabbit Pancreatic Islets in Suspension Culture," J. Cell Biol. 1968, 39(16a).
Asem, E.K. et al. "Effect of Basal Lamina on Progesterone Production by Chicken Granulosa Cells in Vitro—Influence of Follicular Development," Comparative Biochemistry and Physiology, Part C, 125 (2000) pp. 233-244.
Campbell, J.H. et al. "Endothelial Cell Influences on Vascular Smooth Muscle Phenotype," Ann. Rev. Physiol., 1986, vol. 48, 384-91.
Nugent, H.M. et al. "Endothelial Implants inhibit Intimal Hyperplasia After Porcine Angioplasty," Circulation Research, Mar. 5, 1999, 84(4) pp. 384-391.
Hirschi, K.K. et al. "PDGF, TGF-β, and Heterotypic Cell-Cell Interactions Mediate Endothelial Cell-Induced Recruitment of 10T1/2 Cells and Their Differentiation to a Smooth Muscle Fate," The Journal of Cell Biology, 1998. 141(3) pp. 805-814.
Backer, M.P., et al. "Large Scale Production of Monoclonal Antibodies in Suspension Culture," Biotechnology and Bioengineering, 1988, 32, pp. 993-1000.
Badylak, S.T., et al. "Endothelial Cell Adherence to Small Intestinal Submucosa: An Acellular Bioscaffold," Biomaterials, 1999, 20, pp. 2257-2263.
Badylak, S.T., et al. "Directed Connective Tissue Remodeling, Upon a Biologic Collagen Substrate," J. Cell Biochem. 1992, Supplement 16E, Abstract No. CE 027, p. 124.
Bell, et al., "Production of a tissue-like structure by contraction of collagen lattices by human fibroblasts of different proliferative potential in vitro," Mar. 1979, Proc. Natl. Sci. USA, 76(3) pp. 1274-1278.
Bhatia, S.N. et al., "Controlling Cell Interactions by Micropatterning in Co-Cultures: Hepatocytes and 3T3 Fibroblasts," Journal of Biomedical Materials Research, 1997, 34, pp. 189-199.
Bioartificial Organs, Richard Skalak and Fred Fox, eds. Tissue Engineering, Chapter V. Transplants and Artificial Organs, pp. 209, 211-39, and 241-2 (Alan R. Liss, Inc. 1988).
Blay et al., "Epidermal Growth Factor Promotes the Chemotactic Migration of Cultured Rat Intestinal Epithelial Cells," J. Cell Physiology, 1985, 124(1) pp. 107-112.
Block, S., "Peroxygen Compounds," Disinfection, Sterilization and Preservation, 4$^{th}$ Edition 1991, pp. 167-181, Phildelphia, Lea, & Febiger.
Boder, G.B, and Hull, R.H., "Introduction to Techniques in Mammalian Cell Culture," Manual of Industrial Microbiology and Biotechnology, 1983, Ed. A.L. Demain and N.A. Solomon, pp. 248-262.

(56) References Cited

OTHER PUBLICATIONS

Boder, G.B., et al. "Visible Light Inhibits Growth of Chinese Hamster Ovary Cells," European J. Cell Biol., 1983. 31. pp. 132-136.
Boder G.B., et al. "Extended Production of Insulin by Isolated Rabbit Pancreatic Islets; Evidence for Biosynthesis of Insulin," Proc. Soc. Exptl. Biol. Med., 1969, 131, p. 507-513.
Boder, G.B., et al. "Long Term Monolayer Cultures of Islet Cells from Neonatal Mice," J. Cell Biol., 1973, 59, p. 29a.
Boder, G.B., "Mammalian Cell Cultures for Genetically Engineered Products," Toxicologic Pathology, 1989, 17(1) p. 827.
Castano, E., et al., "Inhibition of DNA Synthesis by Aspirin in Swiss 3T3 Fibroblasts," Journal of Pharmacology and Experimental Therapeutics, 1997, 280(1) p. 366-72.
Delcourt-Huard, et al., "Reconstituted Human Gingivial Epithelium: Nonsubmerged in Vitro Model," In Vitro Cellular & Developmental Biology Animal, Jan. 1997, 33(1) p. 30-6.
Deluca, et al., "Evidence That Human Oral Epithelium Reconstituted in Vitro and Transplanted on Patients with Defects in the Oral Mucosa Retains Properties of the Original Donor Site," Transplantation, 1990, 50(3) p. 454-9.
Denton, G.W., "Chlorhexidine," Disinfection, Sterilization and Preservation, 4$^{th}$ Edition 1991, Phildelphia, Lea, & Febiger, p. 274-89.
Elsdale and Bard, "Collagen Substrata for Studies on Cell Behavior," The Journal of Cell Biology, 1972, 54. p. 626-37.
Emerman et al., "Maintenance and Induction of Morphological Differentiation in Dissociated Mammary Epithelium on floating Collagen Membranes," In Vitro, 1977, 13(5) pp. 316-328.
Freed et al., "Joint Resurfacing Using Allograft Chondrocytes and Synthetic Biodegradable Polymer Scaffolds," J. Biomedical Materials Res., 1994, 28, p. 891-9.
Freeman et al., "In vivo-like growth of human tumors in vitro," Proc. Natl. Acad. Sci. USA, Apr. 1986, 83, 2694-8.
Freshney, R.I., "Culture of Animal Cells: A Manual of Basic Technique," Chapters 12 and 13, Alan R. Liss, Inc.. New York (1994) p. 119-43.
Girasole et al., "17-β Estradiol Inhibits IL-6 Production by Bone Marrow-Derived Stromal Cells and osteoblasts in 1 Vitro: A Potential Mechanism for the Antiosteoporotic Effects of Estrogens," The Journal of Clinical Investigation, Inc. 1992, 89, -, 883-91.
Grinnel, "Cell-Collagen Interactions: Overview," Methods in Enzymology, 1982, 82, 499-503.
Hayashi, "The effect of three-dimensional structure of extracellular matrix on cellular functions including response to growth factors," Biophysics, 1992, 32(4) p. 211-5.
Ho, M., et al., "Identification of Endothelial Cell Genes by Combined Database Mining and Microarray Analysis." Physiol, Genomics, 2003, 13, 249-62.
Ibrahiem, E.I.H., et al. "Orthotopic Implantation of Primary N-[4-(5-Nitro-2-furyl)-2-thiazoly]formamide-induced Bladder Cancer in Bladder Submucosa: An Animal Model for Bladder Cancer Study," Cancer Research, 1983, 43. 617-20.
Junnosuke, "Tissue culture-Basics and Applications-," Asakura Publishing Co., Ltd., 1965, p. 31.
Kasitfan, H. et al., "Intra-rectal injection of tumor cells: a novel animal model of rectal cancer," Surgical Oncology, 1992, 1, 251-6.
Keyes, K. et al. "An in Vitro Tumor Model: Analysis of Angiogenic Factor Expression after Chemotherapy." Cancer Research, 2002, 62, 5597-602.
Kleinman, et al., "Preparation of Collagen Substrates for Cell Attachment: Effect of Collagen Concentration and Phosphate Buffer," Analytical Biochemistry, 1979, 94, 308-12.
Kleinman, et al., "Membrane Complexes with Biological Activity," Biochemistry, 1986, 25, 312-8.
Kubota, Y. et al., "Role of Laminin and Basement Membrane in the Morphological Differentiation of Human Endothelial Cells into Capillary-like Structures," Journal of Cell Biology, 1988, 107, 1589-98.
Kuo C.Y., et al., "Biohybrid Islet-Gland Equivalent for Transplantation," Journal of Cellular Biochemistry, Supplement 18C PZ110, Feb. 13-26, 1994.
Kuo, C.Y., et al., "Formation of Pseudoislets from Human Pancreatic Cultures," Pancreas, 1992, 7(3) 320-5.
Larsson, L. et al., "Changes in the Islets of Langerhans in the Obese Zucker Rat," Lab. Invest. 1977, 36, 593-8.
Lee, et al., "Modulation of Secreted Proteins of Mouse Mammary Epithelial Cells by the Collagenous Substrata," The Journal of Cell Biology, 1984, 98, 146-55.
Liu, C. H., et al., "Effects of Salvianolic Acid-A on NIH/3T3 Fibroblast Proliferation, Collagen Synthesis and Gene Expression," World J. Gastroentero, 2000, 6(3) 361-4.
Maru et al., "An Oncogenic Form of the Flt-1 Kinase has a Tubulogenic Potential in a Sinusoidal Endothelial Cell Line," European Journal of Cell Biology, 2000, 79, 130-43.
Michalopoulos & Pitot, "Primary Culture of Parenchymal Liver Cells on Collagen Membranes," Experimental Cell Research, 1975, 94, 70-8.
Mikos, A.G., et al. "Islet Transplantation to Create a Bioartificial Pancreas," Biotech. and Bioengineering, 1994, 43, 673-7.
Mokonjimobe et al., "Hexosaminidase and alkaline phosphatase activities in articular chondrocytes and relationship to cell culture conditions,"Experientia, 1992, 48(4) 396-8.
Nerem, R., "Tissue Engineering: The Hope, The Hype and The Future," Tissue Engineering, 2006, 12(5) 1143-50.
Saltzman et al., "Three-dimensional Cell Cultures Mimic Tissues," Ann, N.Y. Acad. Sci., 1992, 665, 259-73.
Sato et. al., "Artificial Esophagus," Materials Science Forum, 1997, 250, 105-14.
Schor et al., "The Use of Three-Dimensional Collagen Gels for the Study of Tumour Cell Invasion in Vitro: Experimental Parameters Influencing Cell Migration Into the Gel Matrix," Int. J. Cancer, 1982, 29, 57-62.
Shields et al., Invasion of Collagen Gels by Mouse Lympoid Cells, Immunology, 1984, 51, 259-68.
Takahashi, et al., "Compressive force promotes Sox9, type II collagen and aggrecan and inhibits IL-1β expression resulting in chondrogenesis in mouse embryonic limb bud mesenchymal cells," Journal of Cell Science, 1998, 111(14) 2067-76.
Vescoi et al., "In vivo-like drug responses of human tumors growing in three-dimensional gel-supported primary culture," Proc. Natl. Acad. Sci. USA, 1987, 84, 5029-33.
Wakitani et al., "Mesenchymal Cell-Based Repair of Large, Full Thickness Defects of Articular Cartilage," J. Bone Joint Surg. Am., Abstract, 1994, 76(4) 579-92.
Yang, E.K. et al., "Tissue Engineered Artificial Skin Composed of Dermis and Epidermis," International Society for Artificial Organs, 2000, 24(1) 7-17.
Friess, "Collagen-biomaterial for drug delivery," European Journal of Pharmaceutics and Biopharmaceutics 1998, 45(2) 113-36.
Francis, et al. "Endothelial cell-matrix interactions in neovascularization," Tissue Engineering Part B: Reviews, 2008. 14(1) 19-32.
Ruszczak et al., "Effect of collagen matrices on dermal wound healing," Advanced drug Delivery Reviews, 2003, 55.1595-611.
Lillie et al., "Growth of Stratified Squamous Epithelium on Reconstituted Extracellular Matrices: Long-Term Culture," Journal of Investigative Dermatology, 1988, 90(2) 100-9.
Silver et al., "Type I Collagen in Solution," The Journal of Biological Chemistry, 1980, 19(10) 9427-33.
Glowacki, J. and Mizuno, S. "Collagen Scaffolds for Tissue Engineering," Biopolymers, 2007, 89, 338-44.
PCT International Search Report completed by the U.S. Searching Authority dated Nov. 10, 2010 in connection with PCT/US2010/042290.
Sweeney, et al. "Defining the domains of type I collagen involved in heparin-binding and endothelial tube formation." Proceedings of the National Academy of Science, USA 1998, 95, 275-80.
PCT International Search Report for PCT/US2012/040737, dated Dec. 10, 2012, pp. 1-3, issued by the Korean Intellectual Property Office.

(56) References Cited

OTHER PUBLICATIONS

Abou-Neel et al. "Use of multiple unconfined compression for fine control of collagen gel scaffold and mechanical properties," Soft Matter, 2006, 2, 986-92.
Volpi et al. "On adaptive structures of the collagen fibrils of bone and cartilage," J. Biomech, 24 (Suppl I), 1991, 67-77, abstract only.
Zhu et al., "Designed composites for mimicking compressive mechanical properties of articular cartilage matrix," Journal of the Mechanical Behavior of Biomedical Materials, 2014, 36, 32-46.
Mienaltowski, et al. "Structure, Physiology, and Biochemistry of Collagens," Advances in Experimental Medicine and Biology, 2014, 802, 5-29.
International Search Report and Written Opinion issued by the ISA/US, Commissioner for Patents, dated Jan. 19. 2016, for International Application No. PCT/US2015/047176; 12 pages.
Whittington, C., et al., "Oligomers Modulate Interfibril Branching and Mass Transport Properties of Collagen Matrices," Microsc Microanal, Oct. 2013, 19(5) 20 pages.
Shoulders, et al., "Collagen Structure and Stability," Annu. Rev. Biochem., 2009, 78, 929-58.
Blum, K.M., et al., "Acellular and high-density, collagen-fibril constructs with suprafibrillar organization." Biomaterials Science, The Royal Society of Chemistry, 2016, 4, 711-23.
Whittington, C.F., et al., "Collagen-Polymer Guidance of Vessel Network Formation and Stabilization by Endothelial Colony Forming Cells in Vitro," Macromolecular Bioscience, 2013, 13, 1135-49.
Brown, et al., "Ultrarapid Engineering of Biomimetic Materials and Tissues: Fabrication of Nano- and Microstructures by Plastic Compression," Advanced Functional Materials, 2005, 15, 1762-70.
Chicatun, et al., "Osteoid-Mimicking Dense Collagen/Chitosen Hybrid Gels," BioMacromolecules, 2011, 12, 2946-56.
Mitra, et al., "Preparation and characterization of malonic acid cross-linked chitosan and collagen 3D scaffolds: an approach on non-covalent interactions," J. Mater. Sci. Mater Med, 2012, 23, 1309-21.

Zorlutuna et al., "Nanopatterning of Collagen Scaffolds Improve the Mechanical Properties of Tissue Engineered Vascular Graft," Biomacromolecules, 2009, 10, 814-21.
Caves, et al., "Elastin-linke protein matrix reinforced with collagen microfibers for soft tissue repair," Biomaterials. 2011, 32(23) 5371-9.
Shepard, et al., "Effect of fiber crosslinking on collage-fiber reinforced collagen-chondroitin-6-sulfate materials for regenerating load-bearing soft tissues," Journal of Biomedical Materials Research, 2012, 101(1) 176-84.
Hambli et al., "Physically based 3D finite element model of a single mineralized collagen microfibril," Journal of Theoretical Biology, 2012, 301, 28-41.
Ji et al., "Mechanics of electrospun collagen and hydroxyapatite/collagen nanofThers," Journal of the Mechanical behavior of Biomedical Materials, 2012, 13, 185-93.
Grover, et al., "Crosslinking and composition influence the surface properties, mechanical stiffness and cell reactivity of collagen-based films," Acta Biomater, 2012, 8(8) 3080-90.
Kuo Ching Chao et al., "A Novel Human Stem Cell Coculture System that Maintains the Survival and Function of Culture Islet-Like Cell Clusters," Cell Transplantation, Jun. 1, 2008, 657-64.
Brookes, S. et al., "Three-dimensional tissue-engineered skeletal muscle for laryngeal reconstruction: 3D Tissue Engineered Skeletal Muscle," The Laryngoscope, Aug. 26, 2017, 128(3) 603-9.
Wu et al., "Biopringtin three-dimensional cell-laden tissue constructs with controllable degradation," Scientific Reports, 6:24474, Apr. 19, 2016.
Wilson, et al. "A fibril-reinforced poroviscoelastic swelling model for articular cartilage," Journal of biomechanis, 2005, 38(6) pp. 1195-1204.
JPK Instruments, "Collagen: levels of structure and alignment," pp. 1-6, retrieved from the internet 127/2022, https://www.jpk.com/app=technotes-img/AFM/pdf/jpk-app-collagen. 14-1.pdf (Year: 2022).
Merriam-Webster, Engineer definition, retrieved from the internet 127/2022; https://www.merriam-webster.com/dictionaryengineer (Year: 2022).

\* cited by examiner

CELL-COLLAGEN-SILICA COMPOSITES AND METHODS OF MAKING AND USING THE SAME

PRIORITY CLAIM

This application is a U.S. National Stage Application of International Patent Application No. PCT/US2016/028686, filed Apr. 21, 2016, which claims the benefit of U.S. Provisional Patent Application No. 62/150,439, filed Apr. 21, 2015, the entire disclosures of both of which are incorporated by reference herein.

TECHNICAL FIELD

Aspects of the present disclosure generally relate to compositions comprising cells, collagen, and silica, and particularly to a controlled layering of collagen and silica around at least one cell to control pore size and density of the encapsulating material around the at least one cell.

BACKGROUND AND SUMMARY

This section introduces aspects that may help facilitate a better understanding of the disclosure. Accordingly, these statements are to be read in this light and are not to be understood as admissions about what is or is not prior art.

Recent advances in technology have allowed for the integration of man-made substances with cellular materials to create a new class of living composite devices. Such devices have the ability to respond dynamically with biological functionality to their local environment.

Traditionally cell immobilization using sol-gel methods results in cell entrapment within bulk materials creating significant diffusion barriers. Current technology to create thin coatings around cells required aerosolizing processes to apply silica based sol-gels to biological materials. The aerosolizing processes require vaporizing the sol-gel precursors and then contacting the vapor to the cell surface. These processes are inefficient and expensive. In addition only a 2D planar entrapment layer is formed.

Therefore it would be desirable to have a method for forming layers on biological materials and cells which can be tuned, controlled, and replicable, and that is efficient, cost effective, simple, able to create 3D thin layers, and flexible for entrapment of a range of materials from single cells to tissues.

Aspects of the disclosure disclose how oligomeric collagen-fibril matrices with tunable microstructural properties were used to template and direct the formation of biocompatible mesoporous sol-gel silica to produce hybrid organic-inorganic materials. Silica mineralization kinetics is critical for precision-tuning hybrid material properties, including mechanical strength, porous microstructure, depth of silica penetration, and mass transport properties. This work investigates the effect of systematically varying collagen template fibril volume fraction and viscoelasticity, time of contact with silicifying solution, and silicifying solution concentration on the silicification kinetics, hybrid material microstructure, and functionality.

Some aspects of the disclosure provide details on a new composite device comprising at least one cell, a synthesized collagen fibril network, and a silica layer. In certain aspects, a synthetic composite device comprises at least one cell, a collagen network having individual fibril branches, and having an inner portion, and an outer portion, wherein the inner portion is configured to at least partially encapsulate at least one cell, and a silica layer, wherein the silica layer is coupled to the outer portion of the collagen network.

In certain aspects the collagen material is prepared from collagen suspensions, slurries, or solutions. In certain aspects the collagen material is prepared from self-assembling or polymerizable collagens. In certain aspects the collagen material is prepared from oligomers. In certain aspects the collagen fibril network is tuned, engineered or purified collagen from a mammalian source including bovine, porcine, rat, mouse, human, or non-human primate. In certain aspects the tuned, engineered, or purified collagen comprises type I collagen, type II collagen, type IV collagen, or a combination thereof. In certain aspects the shear storage modulus of the collagen network ranges from between 100 Pa to 4000 Pa. In other aspects the shear storage modulus of the collagen network ranges between 100 and 1600 Pa. In other aspects the fibril density of the collagen network is configured to allow a pore size range between about 1 nm to about 1,000 nm. In other aspects the collagen network is configured to allow a pore size ranging between 50 nm and 750 nm.

In certain aspects the at least one cell is a eukaryotic cell. In other aspects the at least one cell is selected from the following, stem cell, pluripotent cell, multipotent cell, totipotent cell, engineered cell, induced pluripotent stem cell, pancreatic cell, epithelial cell, endothelial cell, vascular cell, alpha cell, beta cell, or blood vessel cell. In other aspects the at least one cell may include a plurality of cells organized into tissue groupings such as a pancreatic islet. In other aspects a synthetic composite device may include combinations of at least one cell or a plurality of cells organized into tissue groupings such as a pancreatic islets and vascular cells as a non-limiting example. The number and type of cells included in composite device will depend on a number of factors including mechanical properties of the encapsulating layer including a collagen fibril network and a silica layer. Other factors include application and size of the composite device.

In certain aspects a silica layer is coupled to the collagen network. The silica layer is formed from a silica concentration configured to generate a pore size ranging between about 50 nm to about 750 nm. In other aspects the silica concentration is configured to generate a pore size ranging between about 1 nm to about 1,000 nm. In certain embodiments the silica layer forms only at the surface of the collagen network, coating individual fibrils and avoiding bulk gelation. In certain aspects the silica layer forms at the surface of the outer most layer of the collagen network. In other aspects, the silica layer is generated from a silicifying solution ranging between about 1 vol % to about 10 vol %. In other aspects, the silica layer is generated from a silicifying solution ranging between about 0.5 vol % to about 25 vol %.

In certain aspects, the pore size is selected and configured to selectively diffuse biomolecules and prevent the interaction of the at least one cell with other biomolecules. For instance, it is beneficial to prevent the cells from interacting with antibodies or white blood cells, while still participating in mass transfer of nutrients including oxygen and helpful biomolecules and cell waste. The biomolecules are selected from the a group consisting of steroids, growth factors, transcription factors, proteins, peptides, co-activators, cofactors, sugars, small molecules, lipids, fragments thereof, and combinations thereof. In certain aspects, the pore size is configured to exclude immune cells from coming into contact with the at least one cell.

A first embodiment of the present disclosure includes a composition comprising: at least one biological material; a tuned collagen material comprised of individual fibril branches, and having an inner portion, and an outer portion, wherein the inner portion is configured to at least partially encapsulate the at least one biological material; and a silica layer, wherein the silica layer is coupled to the outer portion of the collagen material.

A second embodiment of the present disclosure includes the first embodiment, wherein the tuned collagen material is self-assembled or polymerized from oligomers.

A third embodiment of the present disclosure includes any one of the first and the second embodiments, wherein the at least one biological material includes at least one biological material selected from the group consisting of: bioelements, biomolecules, biogenic substances, biotic materials, natural materials, bio-based materials, biocompatible materials, biocomposites, biomasses, bodily fluids, cellular components, organic matters, cytokines, tissues, and cells.

A fourth embodiment of the present disclosure includes any one of the first to the third embodiments, wherein the tuned collagen material is derived from type 1 collagen.

A fifth embodiment of the present disclosure includes the fourth embodiment, wherein the type 1 collagen is derived from porcine dermis.

A sixth embodiment of the present disclosure includes any one of the first to the fifth embodiments, wherein the at least one biological material selected from the group consisting of bacterial cells, plant cells, fungal cells somatic cells, stem cells, pluripotent stem cell, induced pluripotent stem cells, multipotent stem cells, totipotent stem cells, genetically engineered cells, pancreatic cells, beta cells, isolated islet cells, tissues, nutrients, enzymes, proteins, cytokines, vasodilators, and vasoconstrictors.

A seventh embodiment of the present disclosure includes any one of the first to the sixth embodiments, wherein the at least one biological material is at least one isolated islet.

An eighth embodiment of the present disclosure includes any one of the first to the seventh embodiments, wherein the at least one biological material is derived from a human or an animal.

A ninth embodiment of the present disclosure includes any one of the first to the eighth embodiments, wherein the shear storage modulus of the tuned collagen material is in the ranges selected from the group consisting of: from about 100 Pa to about 4000 Pa, from about 100 Pa to about 3000 Pa, from about 100 to about 2500 Pa, from about 100 Pa to about 2000 Pa, from about 100 Pa to about 1500, from about 100 Pa to about 1000 Pa, about 100 Pa to about 800 Pa, from about 100 Pa to about 600 Pa, from about 100 to about 400 Pa, from about 100 Pa to about 300 Pa, from about 100 Pa to about 200, from about 200 Pa to about 4000 Pa, from about 200 Pa to about 3000 Pa, from about 200 to about 2500 Pa, from about 200 Pa to about 2000 Pa, from about 200 Pa to about 1500, from about 200 Pa to about 1000 Pa, about 200 Pa to about 800 Pa, from about 200 Pa to about 600 Pa, from about 200 to about 400 Pa, from about 200 Pa to about 300 Pa, 300 Pa to about 4000 Pa, from about 300 Pa to about 3000 Pa, from about 300 to about 2500 Pa, from about 300 Pa to about 2000 Pa, from about 300 Pa to about 1500, from about 300 Pa to about 1000 Pa, about 300 Pa to about 800 Pa, from about 300 Pa to about 600 Pa, from about 300 to about 400 Pa.

A tenth embodiment of the present disclosure includes any one of the first to the ninth embodiments, wherein the fibrillar density of the tuned collagen material is configured to allow a pore size in the ranges selected from the group consisting of: from about 0.1 nm to about 1,000 nm, from about 1 nm to about 900 nm, from about 0.1 nm to about 800 nm, 0.1 nm to about 750 nm, from about 0.1 nm to about 700 nm, from about 0.1 nm to about 500 nm, about 0.1 nm to about 400 nm, from about 0.1 nm to about 300 nm, from about 0.1 nm to about 200 nm, from about 0.1 nm to about 100 nm, from about 0.1 nm to about 50 nm, from about 0.1 nm to about 30 nm, from about 0.5 nm to about 1,000 nm, from about 0.5 nm to about 900 nm, from about 0.5 nm to about 800 nm, from about 0.5 nm to about 750 nm, from about 0.5 nm to about 700 nm, from about 0.5 nm to about 500 nm, about 0.5 nm to about 400 nm, from about 0.5 nm to about 300 nm, from about 0.5 nm to about 200 nm, from about 0.5 nm to about 100 nm, from about 0.5 nm to about 50 nm, from about 0.5 nm to about 30 nm, from about 1 nm to about 1,000 nm, from about 1 nm to about 900 nm, from about 1 nm to about 800 nm, from about 1 nm to about 750 nm, from about 1 nm to about 700 nm, from about 1 nm to about 500 nm, about 1 nm to about 400 nm, from about 1 nm to about 300 nm, from about 1 nm to about 200 nm, from about 1 nm to about 100 nm, from about 1 nm to about 50 nm, from about 1 nm to about 30 nm, 10 nm to about 1,000 nm, from about 10 nm to about 900 nm, from about 10 nm to about 800 nm, from about 10 nm to about 750 nm, from about 10 nm to about 700 nm, from about 10 nm to about 500 nm, about 10 nm to about 400 nm, from about 10 nm to about 300 nm, from about 10 nm to about 200 nm, from about 10 nm to about 100 nm, from about 10 nm to about 50 nm, from about 10 nm to about 30 nm, from 50 nm to about 1,000 nm, from about 50 nm to about 900 nm, from about 50 nm to about 800 nm, 50 nm to about 750 nm, from about 50 nm to about 700 nm, from about 50 nm to about 500 nm, about 50 nm to about 400 nm, from about 50 nm to about 300 nm, from about 50 nm to about 200 nm, and from about 50 nm to about 100 nm.

An eleventh embodiment of the present disclosure includes any one of the first to the tenth embodiments, wherein the silica layer is formed from a silica concentration configured to generate a pore size in the ranges selected from the group consisting of: from about 0.1 nm to about 1,000 nm, from about 1 nm to about 900 nm, from about 0.1 nm to about 800 nm, 0.1 nm to about 750 nm, from about 0.1 nm to about 700 nm, from about 0.1 nm to about 500 nm, about 0.1 nm to about 400 nm, from about 0.1 nm to about 300 nm, from about 0.1 nm to about 200 nm, from about 0.1 nm to about 100 nm, from about 0.1 nm to about 50 nm, from about 0.1 nm to about 30 nm, from about 0.5 nm to about 1,000 nm, from about 0.5 nm to about 900 nm, from about 0.5 nm to about 800 nm, from about 0.5 nm to about 750 nm, from about 0.5 nm to about 700 nm, from about 0.5 nm to about 500 nm, about 0.5 nm to about 400 nm, from about 0.5 nm to about 300 nm, from about 0.5 nm to about 200 nm, from about 0.5 nm to about 100 nm, from about 0.5 nm to about 50 nm, from about 0.5 nm to about 30 nm, from about 1 nm to about 1,000 nm, from about 1 nm to about 900 nm, from about 1 nm to about 800 nm, from about 1 nm to about 750 nm, from about 1 nm to about 700 nm, from about 1 nm to about 500 nm, about 1 nm to about 400 nm, from about 1 nm to about 300 nm, from about 1 nm to about 200 nm, from about 1 nm to about 100 nm, from about 1 nm to about 50 nm, from about 1 nm to about 30 nm, 10 nm to about 1,000 nm, from about 10 nm to about 900 nm, from about 10 nm to about 800 nm, from about 10 nm to about 750 nm, from about 10 nm to about 700 nm, from about 10 nm to about 500 nm, about 10 nm to about 400 nm, from about 10 nm to about 300 nm, from about 10 nm to about 200 nm, from about 10 nm to about 100 nm, from about 10 nm to about 50 nm, from about 10 nm to about 30 nm, from about 50 nm to about 1,000 nm, from about 50 nm to about 900 nm, from about 50 nm to about 800 nm, 50 nm to about 750 nm, from about 50 nm to about 700 nm, from about 50 nm to about 500 nm, about 50 nm to about 400 nm, from about 50 nm to about 300 nm, from about 50 nm to about 200 nm, and from about 50 nm to about 100 nm.

A twelfth embodiment of the present disclosure includes any one of the first to the eleventh embodiments, wherein the silica layer forms at the surface of the tuned collagen material.

A thirteenth embodiment of the present disclosure includes any one of the first to the twelfth embodiments, wherein the silica layer forms on the individual fibril branches of the collagen network.

A fourteenth embodiment of the present disclosure includes any one of the first to the thirteenth embodiments, wherein the pores are configured to selectively diffuse biomolecules.

A fifteenth embodiment of the present disclosure includes the fourteenth embodiments, wherein biomolecules are selected from the group consisting of steroids, growth factors, transcription factors, proteins, peptides, co-activators, cofactors, sugars, small molecules, lipids, fragments thereof, and combinations thereof.

A sixteenth embodiment of the present disclosure includes any one of the first to the fifteenth embodiments, wherein immune cells are excluded from interacting with the at least one cell.

A seventeenth embodiment of the present disclosure includes any one of the first to the sixteenth embodiments, wherein the silica layer is generated from a silicifying solution in the ranges selected from the group consisting of: from about 1 vol % to about 20 vol %, about 1 vol % to about 15 vol %, about 1 vol % to about 10 vol %, 1 vol % to about 6 vol %, about 1 vol % to about 3 vol %, 3 vol % to about 20 vol %, about 3 vol % to about 15 vol %, about 3 vol % to about 10 vol %, and about 3 vol % to about 6 vol %.

An eighteenth embodiment of the present disclosure includes a method for making a silicified tuned collagen material, comprising the steps of: creating a tuned collagen material, having a first surface and a second surface; exposing said tuned collagen material to a silicifying solution to form a silicified tuned collagen material; and washing said tuned collagen material with at least one buffer which stops the silicifying process. In some other embodiments, the exposing step continues for a predetermined time based on expected kinetic rate determined from correlations with collagen properties and desired end properties of silica/collagen composite. In other embodiments, the silicifying solution is an aqueous solution containing silicic acid precursors (any silicic acid composed of e.g. Si(OH)4, or Si(OH)3-R, where R is any organic group including peptides). Yet another embodiment includes the washing step further including the step of removing silicifying solution after predetermined time, and replacing the silicifying solution with non-silicifying fluid (e.g., water or aqueous buffer). Yet another embodiment includes the step of adding ions (e.g., phosphate) to silicifying solution to influence kinetics of formation and/or the final properties.

A nineteenth embodiment of the present disclosure includes the eighteenth embodiment, wherein the tuned collagen material is created by polymerizing isolated collagen monomer to form a tuned collagen material having a desired collagen fibril density.

A twentieth embodiment of the present disclosure includes any one of the eighteenth to the nineteenth embodiment, wherein the tuned collagen material exhibits G' value selected from the ranges consisting of: from about 100 Pa to about 4000 Pa, from about 100 Pa to about 3000 Pa, from about 100 to about 2500 Pa, from about 100 Pa to about 2000 Pa, from about 100 Pa to about 1500, from about 100 Pa to about 1000 Pa, about 100 Pa to about 800 Pa, from about 100 Pa to about 600 Pa, from about 100 to about 400 Pa, from about 100 Pa to about 300 Pa, from about 100 Pa to about 200, from about 200 Pa to about 4000 Pa, from about 200 Pa to about 3000 Pa, from about 200 to about 2500 Pa, from about 200 Pa to about 2000 Pa, from about 200 Pa to about 1500, from about 200 Pa to about 1000 Pa, about 200 Pa to about 800 Pa, from about 200 Pa to about 600 Pa, from about 200 to about 400 Pa, from about 200 Pa to about 300 Pa, 300 Pa to about 4000 Pa, from about 300 Pa to about 3000 Pa, from about 300 to about 2500 Pa, from about 300 Pa to about 2000 Pa, from about 300 Pa to about 1500, from about 300 Pa to about 1000 Pa, about 300 Pa to about 800 Pa, from about 300 Pa to about 600 Pa, from about 300 to about 400 Pa, about 100 Pa, about 200 Pa, about 300 Pa, about 400 Pa, about 500 Pa, about 600 Pa, about 700 Pa, about 800 Pa, about 900 Pa, about 1000 Pa, about 1100 Pa, about 1200 Pa, about 1300 Pa, about 1400 Pa, about 1500 Pa, about 1600 Pa, about 1700 Pa, about 1800 Pa, about 1900 Pa, about 2000 Pa, about 2500 Pa, about 3000 Pa, about 3500 Pa, and about 4000 Pa.

A twenty first embodiment of the present disclosure includes any one of the eighteenth to the twentieth embodiments, wherein the silicifying solution is formed by: hydrolyzing tetramethoxysilane hydrolyzed under acidic conditions in water; and removing most if not all of the methanol by product.

A twenty second embodiment of the present disclosure includes any one of the eighteenth to the twenty first embodiments, wherein said exposing step is a two-phase process including a Phase 1 condensation step and a Phase 2 condensation step, wherein the initial rate of the Phase 1 surface condensation exceeds the rate of the Phase 2 bulk condensation step to form a continuous mineral layer on the first surface of the tuned collagen material.

A twenty third embodiment of the present disclosure includes any one of the eighteenth to the twenty second embodiments, further including contacting the second surface of the tuned collagen material with at least one biological material selected from the group consisting of bacterial cells, plant cells, fungal cells somatic cells, stem cells, pluripotent stem cell, induced pluripotent stem cells, multipotent stem cells, totipotent stem cells, genetically engineered cells, pancreatic cells, beta cells, isolated islet cells, tissues, nutrients, enzymes, proteins, cytokines, vasodilators, and vasoconstrictors.

A twenty fourth embodiment of the present disclosure includes any one of the eighteenth to the twenty third embodiments, wherein the collagen rich solution comprises individual fibril matrices with fibrillary densities selected from the group consisting of: from about 100 Pa to about 4000 Pa, from about 100 Pa to about 3000 Pa, from about 100 to about 2500 Pa, from about 100 Pa to about 2000 Pa, from about 100 Pa to about 1500, from about 100 Pa to about 1000 Pa, about 100 Pa to about 800 Pa, from about 100 Pa to about 600 Pa, from about 100 to about 400 Pa, from about 100 Pa to about 300 Pa, from about 100 Pa to about 200, from about 200 Pa to about 4000 Pa, from about 200 Pa to about 3000 Pa, from about 200 to about 2500 Pa, from about 200 Pa to about 2000 Pa, from about 200 Pa to about 1500, from about 200 Pa to about 1000 Pa, about 200 Pa to about 800 Pa, from about 200 Pa to about 600 Pa, from about 200 to about 400 Pa, from about 200 Pa to about 300 Pa, 300 Pa to about 4000 Pa, from about 300 Pa to about 3000 Pa, from about 300 to about 2500 Pa, from about 300 Pa to about 2000 Pa, from about 300 Pa to about 1500, from about 300 Pa to about 1000 Pa, about 300 Pa to about 800 Pa, from about 300 Pa to about 600 Pa, from about 300 to about 400 Pa, about 100 Pa, about 200 Pa, about 300 Pa, about 400 Pa, about 500 Pa, about 600 Pa, about 700 Pa, about 800 Pa, about 900 Pa, about 1000 Pa, about 1100 Pa, about 1200 Pa, about 1300 Pa, about 1400 Pa, about 1500 Pa, about 1600 Pa, about 1700 Pa, about 1800 Pa, about 1900 Pa, about 2000 Pa, about 2500 Pa, about 3000 Pa, about 3500 Pa, and about 4000 Pa.

A twenty fifth embodiment of the present disclosure includes any one of the eighteenth to the twenty fourth embodiments, wherein the silicifying solution has a concentration in the ranges selected from the group consisting of: from about 1 vol % to about 20 vol %, about 1 vol % to about 15 vol %, about 1 vol % to about 10 vol %, 1 vol % to about 6 vol %, about 1 vol % to about 3 vol %, 3 vol % to about 20 vol %, about 3 vol % to about 15 vol %, about 3 vol % to about 10 vol %, and about 3 vol % to about 6 vol %.

A twenty sixth embodiment of the present disclosure includes any one of the eighteenth to the twenty fifth embodiments, wherein the at least one biological material is derived from an animal or a human.

A twenty seventh embodiment of the present disclosure includes a method of treating a patent, comprising the steps of: treating a patient with any of silicified tuned collagen materials of any one of the first to twenty sixth embodiments.

A twenty eighth embodiment of the present disclosure includes a kit, comprising: at least one type of isolated collagen monomer; a silicifying solution; and a polymerization buffer; wherein the polymerization buffer comprises a phosphate buffer having a pH of about 7.0 to about 8.0 or a pH of about 7.2 to about 7.6.

A twenty ninth embodiment of the present disclosure includes the twenty ninth embodiment, the kit further comprises a phosphate buffer solution; a glucose solution; a calcium chloride solution; an acid solution; and a basic neutralizing solution.

A thirtieth embodiment of the present disclosure includes any one of the twenty eighth to the twenty ninth embodiments, wherein the kit comprises three-dimensional, preformed silicified tuned collagen materials of any one of the first to twenty sixth embodiments.

DETAILED DESCRIPTION

Figure 1:
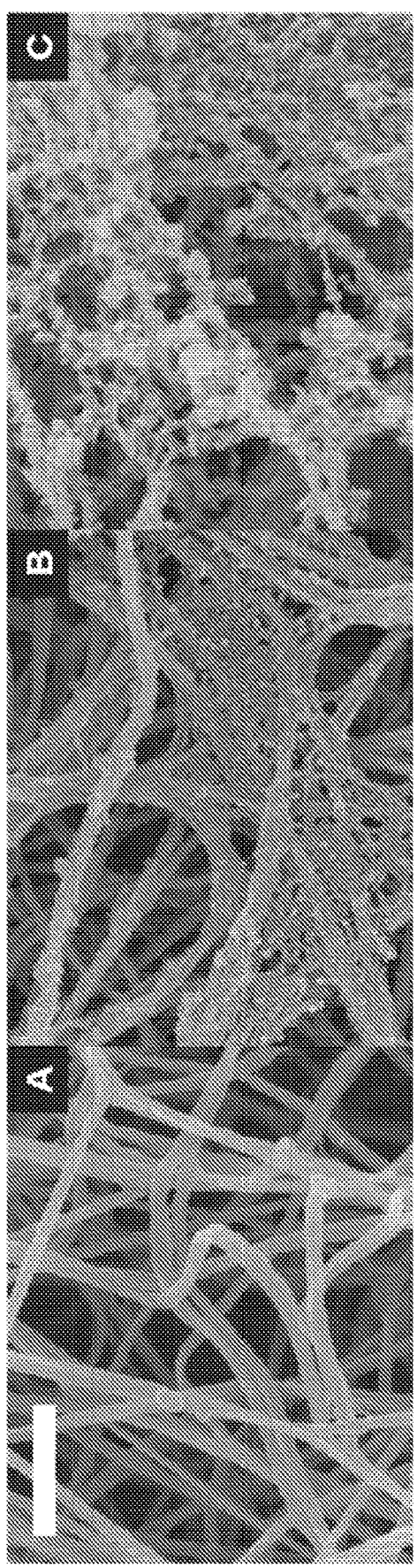
FIG. 1A. Scanning Electron Micrograph (SEM) images showing the image of collagen fibrils not exposed to a silicifying solution.
FIG. 1B. SEM images showing collagen fibril material exposed to 3 volume percent solution (3 vol. %) for 15 minutes (min).
FIG. 1C. SEM images showing a collagen fibril material exposed to 3 volume percent solution (3 vol. %) for 30 minutes (min).

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

"Bulk gelation" refers to a continuous matrix of silica formed independently of the surface of the collagen network individual branches.

"Tuned collagen material" generally refers to an insoluble, highly-branched collagen-fibril matrix formed or synthesized via macromolecular self-assembly of soluble collagen precursors, with multi-scale properties, including fibril microstructure, viscoelasticity, and proteolytic degradability, that are defined by collagen precursor composition and self-assembly reaction conditions. Soluble collagen precursors can be recovered from sources such as processed porcine dermis or any other animals. Soluble collagen precursors can be produced recombinantly or synthetically created via de novo synthesis using appropriate amino acids and polypeptides known in the art. Tuned collagen materials can be created from soluble collagen precursors that are derived from various animal sources or from collagen precursors produced recombinantly or synthetically, or in combination thereof.

"Biological material" refers to any material including, but not limited to, a chemical substance (elements or compounds) or mixture of substances, present or produced in a living organism, being ionic or not, molecular or a non-bonded atom (monatomic), an inorganic or an organic compound. For example, biological materials include, but are not limited to, bioelements, biomolecules (e.g., cytokines), biogenic substances, biotic materials, natural materials, bio-based materials, biocompatible materials, biocomposites, biomasses, bodily fluids, cellular components, organic matters, tissues, or cells.

The term "lyophilized" means that water is removed from the composition, typically by freeze-drying under a vacuum. However, lyophilization can be performed by any method known to the skilled artisan and the method is not limited to freeze-drying under a vacuum.

As used herein, "isolated collagen" means any type of collagen, naturally present in a collagen-containing source material (described below) wherein the collagen has been at least partially purified by isolation and removal from the collagen-containing source material.

As used herein collagen "oligomer(s)" means covalently cross-linked collagen monomers (e.g., dimers=2 monomers, trimers=3 monomers, etc.).

Unless specifically or implicitly stated otherwise the term 'about' as used herein means plus or minus 10 percent. For example, 'about 1.0' encompasses the range of 0.9 to 1.1.

Porous coatings at the surface of living cells have application in human cell transplantation by controlling the transport of biomolecules to and from the cells. Sol-gel-derived mesoporous silica materials are good candidates for such coatings, owing to their biocompatibility, facile solution-based synthesis conditions, and thin film formation. Diffusion and transport across the coating correlates to long-range microstructural properties, including pore size distribution, porosity, and pore morphology.

Porous silica encapsulation of cells may result in material properties with specific advantages for the application to cellular transplant therapies. First, silica sol-gels are bioactive materials that integrate with the surrounding tissue forming a biocompatible interface. This interaction with native tissues prevents the formation of a thick capsule that can limit diffusion, reducing the efficacy of transplanted tissue. Second, the resulting materials may possess high pore volumes but with mesoscale pore sizes (2-50 nm) similar to those produced by solution sol-gel methods thus enabling good transport of small molecules through the materials while securely encasing cells. Third, swelling of a cell immobilization matrix can result in cell loss. Unlike immobilization using soft materials, such as hydrogels, the porous silica layers will not swell; therefore cell entrapment is maintained over time. Fourth, because the sol-gel synthesis results in the formation of a solid matrix from liquid precursors, the solid can be formed on complex geometries. This feature will be extremely useful for coating suspended cells or cells cultured on or within 3D scaffolds or matrices. Fifth, the thickness of the biomineral layer can be controlled by the duration of exposure to the mineralizing environment. Films may range in thickness from 100-200 nm to several microns. Compared to bulk materials, thin (nano) and thick (micro) films have the advantage of not creating additional diffusion barriers that could limit transport. Sixth, the breakdown product of silica-based biominerals is primarily silicic acids. These small molecules are naturally occurring in many organs (including bone, kidneys, liver) and are well tolerated by living organisms including humans. Finally, silica biomaterials have good optical properties in the UV and visible spectra allowing for characterization and monitoring of the underlying cells and substrates. See U.S. Pat. No. 8,183,043, U.S. Patent Publication Nos. 2012/0178137 and 20140363872, disclosures of which are incorporated by reference in its entirety to the extent they are not inconsistent with the explicit teachings of this specification.

It has been found that the proteins and carbohydrates on the cell surface serve as nucleation points for the deposition of silica, causing the formation of a mesoporous amorphous silica glass around the cells. In silica-containing buffered media, silica is attracted to the cell membrane, forming a sol-gel layer. The sol-gel layer continues the polycondensation of the silica particles in the sol-gel to form the silica glass layer around the cells. The natural concentration of the silica sol-gel on the cell membrane allows for the polycondensation of the silica particles in the sol-gel to form the silica glass layer around the cells without having to remove the solvent. See U.S. Patent Publication No. 2012/0178137, disclosures of which are incorporated by reference in its entirety to the extent they are not inconsistent with the explicit teachings of this specification.

The ability to control the process of how collagen interfaces with living cells and living tissues as well has how silica interacts with collagen is central to fully developing this technology. The ability to produce tunable collagen matrices and other tunable collagen based materials is essential to optimizing the interaction of collagen materials with both living cells and/or living tissue and controlling the structure and properties of any silica units and/or surfaces attached to or otherwise in communication with the particular collagen material.

Single collagen molecules (referred to as monomers or telocollagen) are comprised of two $\alpha 1$ polypeptide subunits and one $\alpha 2$ polypeptide subunit. Oligomers, on the other hand, represent two or more monomers held together by covalent crosslinks, such as enzymatically catalyzed aldol, hydroxyaldol, and ketoimine linkages. The tissue-specific microstructure and mechanical properties of collagen matrices are determined by the type and number of collagen molecule crosslinks as well as the ratio of monomers to oligomers, and average molecular weight of collagen molecules.

Some of the properties that influence the mechanical and chemical properties of commercial and many laboratory-generated collagen formulations are difficult to standardize for side-by-side comparison. Differences in commercial preparation, even on a batch-by-batch basis from the same company, make reproducibility in creating collagen matrices extremely difficult, if not impossible. These disadvantages must be overcome in order to reliably produce and systematically vary the collagen matrix material properties. Therefore, to understand the interactions that occur between fibrillar collagen matrices and condensing silicic acids, this research employs an uncommon set of porcine tissue-derived soluble type I collagen oligomers, which maintain their telopeptide sequences and are specified by their intermolecular crosslink composition. The high level of tunability possible for oligomeric collagen fibril matrices enables careful design of experiments as well as reliable and robust engineering and manufacturing of composite devices Oligomers, which represent soluble aggregates of tropocollagen molecules (e.g., trimers) that retain their natural intermolecular crosslinks exhibit not only fibrillar but also suprafibrillar assembly. Unlike conventional collagen monomers (atelocollagen and telocollagen), which form entangled networks of long individual fibrils, oligomers yield highly interconnected collagen-fibril matrices with dramatically improved mechanical integrity and handling as well as reduced proteolytic degradation. The hierarchical self-assembly of soluble collagen oligomers to form fibrils and fibril networks is spontaneous under neutral conditions at 37° C. and stabilized by inter- and intramolecular crosslinking. Furthermore, oligomers are standardized based on their polymerization or matrix-forming capacity, thereby yielding highly reproducible relationships between oligomer concentration of the polymerization reaction, fibril density, and shear storage modulus (stiffness) of formed matrices.

One of the strategies exploited and discussed herein to produce tuned collagen silica materials includes controlling the interaction between condensing silicic acid mineral phase and the collagen-fibril template organic phase employs an uncommon formulation of soluble type I collagen oligomers. The tunability of fibril microstructure afforded by this collagen system is preserved in the templated silica layer, implying a relationship between collagen fibril density and silica nucleation potential. See Kahn J. L. et al., *Collagen-fibril matrix properties modulate the kinetics of silica polycondensation to template and direct biomineralization*, J. MATER. RES., vol. 31, no. 3, Feb. 15, 2016, p. 311-320, disclosures of which are incorporated by reference in its entirety to the extent they are not inconsistent with the explicit teachings of this specification.

The benefit of controlling silica condensation rates at the surface of collagen-fibril templates extends across several active areas of research, including cellular microencapsulation, bone and tissue engineering, and biomineralization. In theory, bulk solution and surface gelation rates should have a synergistic influence on hybrid material properties like mineral layer thickness and depth of penetration, while pore size distribution and porosity are controlled both at the level of the collagen-fibril template and silica formation. One aspect of the present disclosure includes the study of sol-gel silica condensation kinetics during interaction with collagen-fibril templates with systematically varied fibril densities. Chemical and rheological analyses provide insight into reaction rates at the surface of the template and in the surrounding bulk solution, leading to a proposed two-phase gelation process describing high initial rates of gelation at the surface that decrease over time in contrast with low initial rates of bulk gelation that increase over time.

Some embodiments of the present disclosure relates to the technology to enable cell transplantation as a treatment for patients with various diseases including, but not limited to, type 1 diabetes (T1D), cancers, cardiovascular diseases, and pancreatic diseases. T1D is an autoimmune disease characterized by the targeted destruction and dysfunction of islets. Islets are tissue structures in the pancreas that contain β cells, which release insulin in response to glucose. Patients with T1D must tightly monitor and control their blood glucose levels with injected insulin in order to survive.

While insulin injection is the standard of care for patients with T1D, insulin therapy is an inferior control system compared to BioSilica-islet Technology and cannot prevent the long-term chronic complications that contribute to high medical costs, reduced quality of life and reduced life expectancy (Table 1). Transplantation of replacement islets could eliminate the need for insulin injection and long-term complications, but the new islets must be protected from destruction by the on-going autoimmune response. Encapsulation with a protective, selectively porous material, could allow transplanted islets or insulin producing beta cells to survive long-term thereby becoming a transformative treatment for patients with T1D.

TABLE 1

Summary Comparison of BioSilica-Islet Technology to Current Gold Standard Technology.

| | Gold Standard: Insulin Injections | BioSilica-Islet Technology |
|---|---|---|
| Glycemic Control | Highly dependent on patient compliance; Tight control risks hypoglycemic events | Enduring glycemic control; Low dependence on patient compliance |
| Morbidity | Microvascular and macrovascular pathologies; e.g., retinopathy nephropathy | Eliminate/Reduce cormobidities; about 30-35% decrease in morbidity risk with 1% decrease in HbAc1 |

TABLE 1-continued

Summary Comparison of BioSilica-Islet Technology to Current Gold Standard Technology.

| | Gold Standard: Insulin Injections | BioSilica-Islet Technology |
|---|---|---|
| Quality of Life | Injections Daily | One or few injections in lifetime |
| Risk | Risk from non-compliance; Chronic complications | Procedure risk; Immune rejection |
| Cost | About $14,000 direct annual cost | One time cost |

The natural polymer collagen has been shown to template and direct silica condensation. Collagen is an excellent candidate protein to study silica templating kinetics, owing to its natural abundance, regular structure, and relevance to human physiology. The primary structure of collagen is high in repetitive (Gly-Xaa-Yaa)$_n$ triplets with hydroxylation at the Yaa position, often (Gly-Pro-Hyp)$_n$. Multiple hydroxylation sites in close proximity are uniquely capable of interacting with silicic acids, as evidenced by molecular modeling and increased condensation rates for specialized sponge collagen motifs where Xaa is hydroxylated in addition to Yaa. Amines present in abundant Arg, Lys, and Gln residues can take part in cooperative interactions with hydroxyls to affect kinetic drivers for silica condensation.

For additional background information about engineered ECM scaffolds, 3D purified collagen matrices, and collagen preparations, see published International Application Nos. WO2006124946, WO2007136634, and WO2008036393, disclosures of all which are incorporated by reference in its entirety to the extent they are not inconsistent with the explicit teachings of this specification. Also see Kreger S. T. et al, *Polymerization and Matrix Physical Properties as Important Design Considerations for Soluble Collagen Formulations*, BIOPOLYMERS, vol. 93, no. 8, 2010, pp. 690-707, and Voytik-Harbin S. L., *Collagen-Cell Interaction in Three-Dimensional Microenvironments*, HANDBOOK OF IMAGING IN BIOLOGICAL MECHANICS, 2014, pp. 257-269, disclosures of all which are incorporated by reference in its entirety to the extent they are not inconsistent with the explicit teachings of this specification.

An engineered tissue composite comprising therapeutic cells (for example but not limited to stem cell derived insulin producing cells) contained within a collagen-fibril based extracellular matrix and further coated with a surface or penetrating silica coating. Properties of the self-assembled or polymerizable collagen materials, including fibril microstructure (i.e., density, fibril branching), proteolytic degradability, and mechanical properties, are tuned to improve cell health, maintenance of phenotype and function, as well as provide a template to better control silica pore size. Collagen maximizes cell health, provides a tissue microenvironment that supports cell phenotype and function, and provides a tunable surface to better control silica pore size. The silica pore size is designed to control transport of beneficial molecules in and out of the composite and prevent access from harmful molecules (e.g. inflammatory molecules in the case of type 1 diabetes). The silica may be organically modified to further enhance transport based protection and/or to improve biocompatibility by control of physico-chemical parameters (e.g. surface charge, hydrophilicity/hydrophobicity) and presentation of bioactive molecules (peptide receptor ligands) or biomolecules.

Referring now to FIG. 1A-C, SEM images (150,000×, scale bar 500 nm) for 200 Pa collagen matrices not exposed to silicifying solution (FIG. 1A), exposed to 3 vol % silicifying solution for 15 min (FIG. 1B), and 30 min (FIG. 1C) demonstrate the coating of individual collagen fibrils. Silica condensation conditions in the present study are characterized by lack of precursor stabilization, removal of methanol hydrolysis byproduct, relatively short gelation time-scale, and high concentration of silicic acid.

Still referring to FIG. 1, networks of collagen fibrils served as an effective template for condensing silica particles. Prior to gelation of the bulk silicifying solution, fibrils at the surface of the collagen matrix serve as nucleation sites for polycondensation of silica. The results visualized in FIG. 1 were generated using a templating mechanism with a 200 Pa collagen matrix that has been silicified for two time points with a constant concentration of silicic acid (15, 30 min using 3 vol % in 1×PBS) and compared to a non-silicified control (FIG. 1A). Silica particles of approximately 20 nm diameter form at the surface of the collagen and web together (FIG. 1B), eventually forming a more developed porous silica layer (FIG. 1C). As the condensation process proceeds, longer exposure time corresponds to a more advanced formation of the porous silica coating, but the silicifying solution is removed before gelation in the bulk is allowed to continue.

Because silica forms at the surface of individual collagen fibrils, the microstructural properties of the starting collagen template are preserved in the final silica-collagen composite. Comparison of varied collagen fibril densities for the same time and concentration of silica exposure confirms that increased collagen fibril density leads to decreased silica pore sizes.

Figure 2:
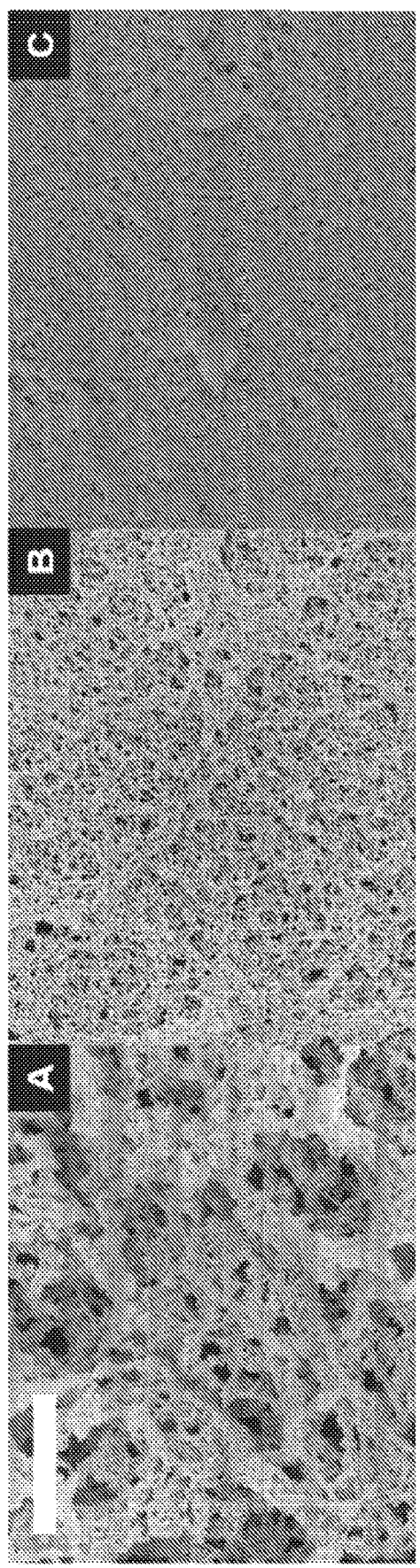
FIG. 2A. SEM images showing silica coating microstructure formed for 100 Pa.
FIG. 2B. SEM images showing silica coating microstructure formed for 100 Pa.
FIG. 2C. SEM images showing silica coating microstructure formed for and 1600 Pa.

Referring now to FIGS. 2A-C. SEM images (20,000×, scale bar 4 μm) for 200 Pa (FIG. 2A), 1000 Pa (FIG. 2B), and 1600 Pa (FIG. 2C). The collagen samples were exposed to 3 vol % silicifying solution for 45 min demonstrate trend of decreasing silica pore size with increasing collagen fibril density. These images of collagen matrix fibril density show that fibril density modulates silica coating microstructure; these results are consistent with the controlled changes in silica surface structure in response to three different collagen fibrillar densities (corresponding to calibrated stiffness of 200, 1000, 1600 Pa) for constant silicifying conditions (45 min exposure, 3 vol % silicic acid in 1×PBS). Lower fibrillar densities, which correlate directly to low matrix shear storage modulus values, have larger void areas between individual fibrils, which leads to looser silica networks with larger pores. Higher fibrillar density networks yield silica networks with smaller pores. This trend is reproducible, even when collagen matrices are exposed to a higher silicic acid concentration (6 vol % silicifying solution, data not shown).

Figure 3:
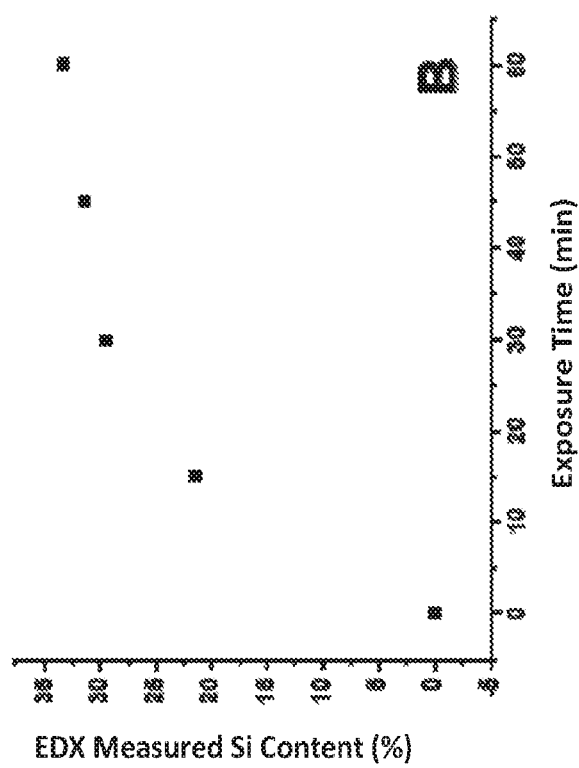
FIG. 3A. A graph illustrating EDX measured Si content measured at various silica acid concentrations (vol %).
FIG. 3B. A graph illustrating EDX measured Si content measured at various exposure times (min).
Figure 3:
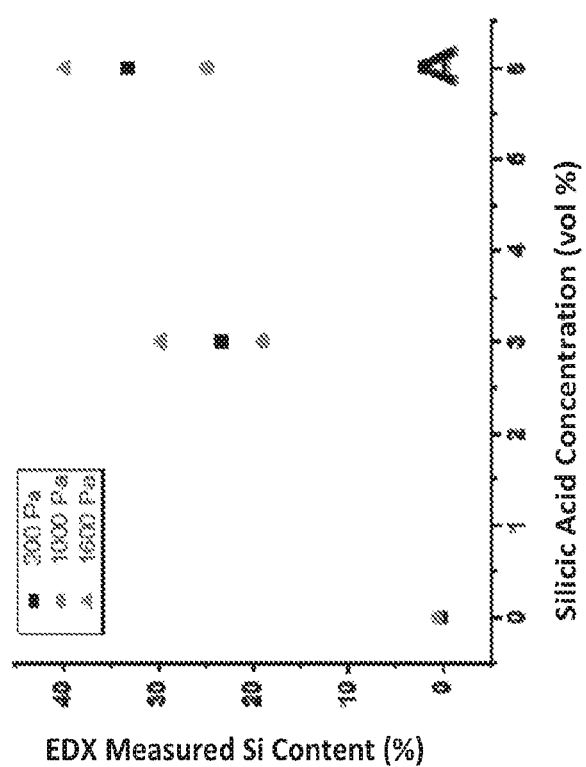

Hybrid materials can be further tuned by adjusting the silicic acid concentration and time of exposure. Relative to collagen content, silica content increases with higher silicic acid concentrations and with longer times of exposure to silicifying solution. Referring now to FIGS. 3A-B, elemental analysis for three different collagen densities exposed to silicifying solution for a constant exposure time (15 min) indicates trend of increasing silica content with increased exposure concentration (n=1) (FIG. 1A). Elemental analysis for 1600 Pa collagen matrices indicates a trend of increasing silica content with increased exposure time (n=1) (FIG. 1B). These images appear to demonstrate that Silica deposition increases with increasing silicic acid concentration and silicification time. The image of FIG. 3A provides elemental analysis (EDX) for samples silicified at three different silicifying concentrations (0, 3, 6 vol %), three different collagen stiffnesses (200, 1000, 1600 Pa), and a constant 15 min exposure time. While FIG. 3B, provides elemental analysis (EDX) of one 1600 Pa collagen sample silicified with 3 vol % silicic acid; data collected at five different exposure time points (0, 15, 30, 45, 60 min).

Although the observed trend of increased relative silica content for increasing silicifying concentrations during a constant time is clear, each sample was evaluated at a single representative site, so individual collagen densities cannot be compared with statistical certainty. Future experiments that compare samples at multiple sites may in fact show no statistical difference; silica that deposits on individual collagen fibrils should maintain the same silica to collagen ratio independent of the number of fibrils present. Varying the exposure time is another effective tool for controlling silica content in the composite. Without removal of the bulk silicifying solution, we expect that this trend should continue until bulk gelation completely surrounds the collagen in a solid silica matrix. Again, individual collagen treatments should maintain statistically similar silica to collagen ratios throughout. Mechanical properties of hybrid materials are dominated by silica content.

Figure 4:
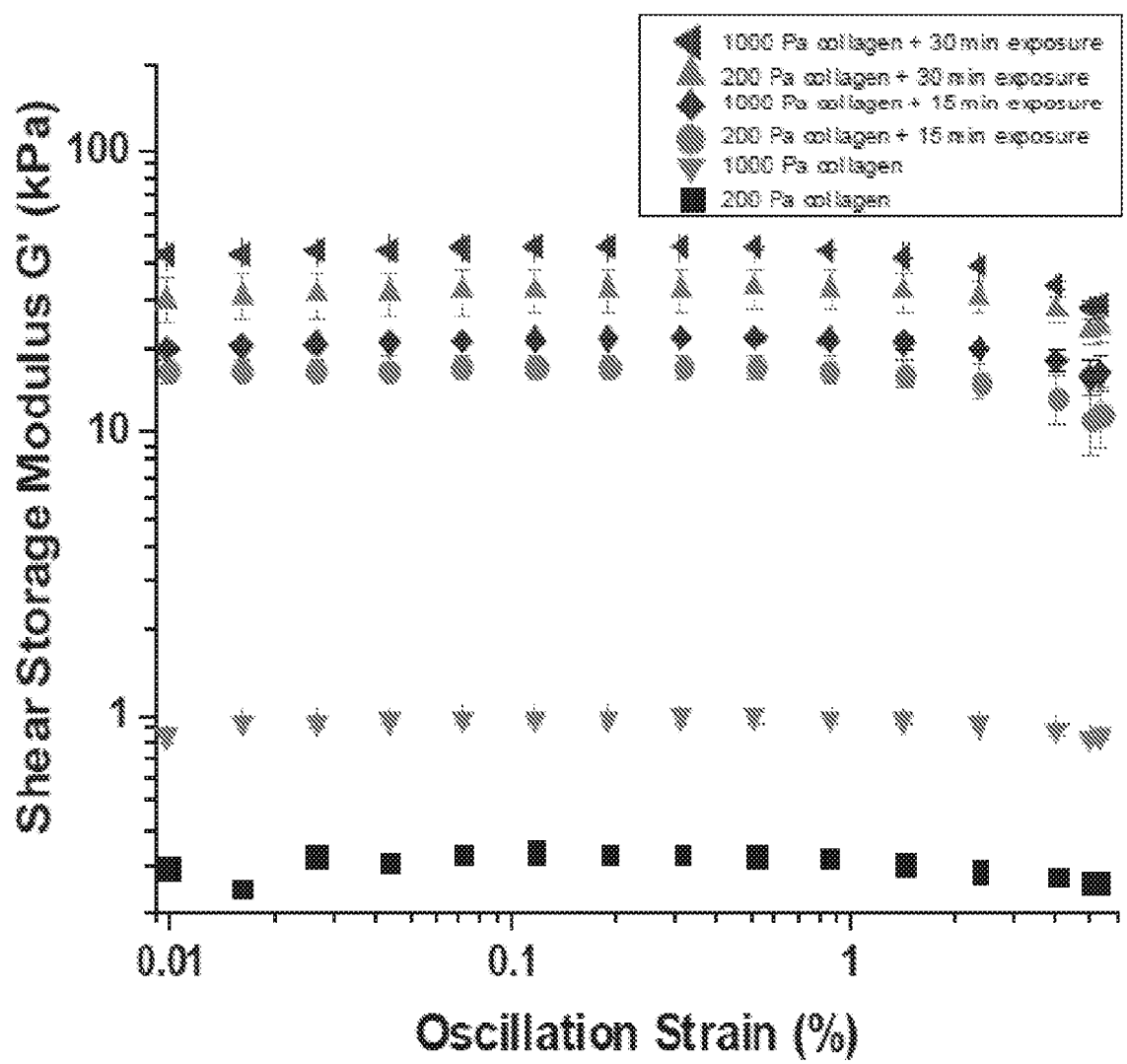
FIG. 4. A graph showing Shear Storage Modulus G' (kPa) measured as function of Oscillation Strain (%).

Referring now to FIG. 4, tuned silicified collagen-fibril matrices exhibit significantly higher shear storage moduli (G') compared to non-silicified collagen controls. Higher collagen fibril density and higher time of exposure to silicifying solution contribute respectively to increased absolute and relative silica content, which corresponds to larger shear storage moduli. Shear storage moduli (G') recorded by a rotational rheometer. These experiments were conducted over a strain range of 0.01-5% at 1 Hz constant frequency for two collagen stiffnesses (200, 1000 Pa) exposed to 3 vol % silicifying solution for three times (0, 15, 30 min). Error bars indicate standard error of the mean based on at least two independent samples, with the exception of 200 Pa control (n=1). Non-silicified collagen controls exhibit the expected shear storage moduli as determined by previous quality control. See Bailey, P. J. Critser, C. Whittington, J. L. Kuske, M. C. Yoder, and S. L. Voytik-Harbin, *Biopolymers*, 95, 77-93 (2011).

The data presented in FIG. 4 indicate that tuned silicified collagen-fibril matrices exhibit significantly higher shear storage moduli (G') compared to non-silicified collagen controls. Higher collagen fibril density and higher time of exposure to silicifying solution contribute respectively to increased absolute and relative silica content, which corresponds to larger shear storage moduli.

Tuned silicified collagen samples exhibit G' dependence on the absolute amount of silica present, where higher collagen fibril density (i.e., higher initial collagen stiffness) relates to greater amounts of silica in the composite. Tuned silicified collagen samples also exhibit G' dependence on the amount of silica present relative to the amount of collagen present, where longer silica exposure times relate to greater amounts of silica per collagen fibril in the composite; this result is in agreement with previously discussed elemental analysis (FIG. 3A). All tuned silicified collagen samples are characterized by far higher G' values than their corresponding collagen controls.

Figure 5:
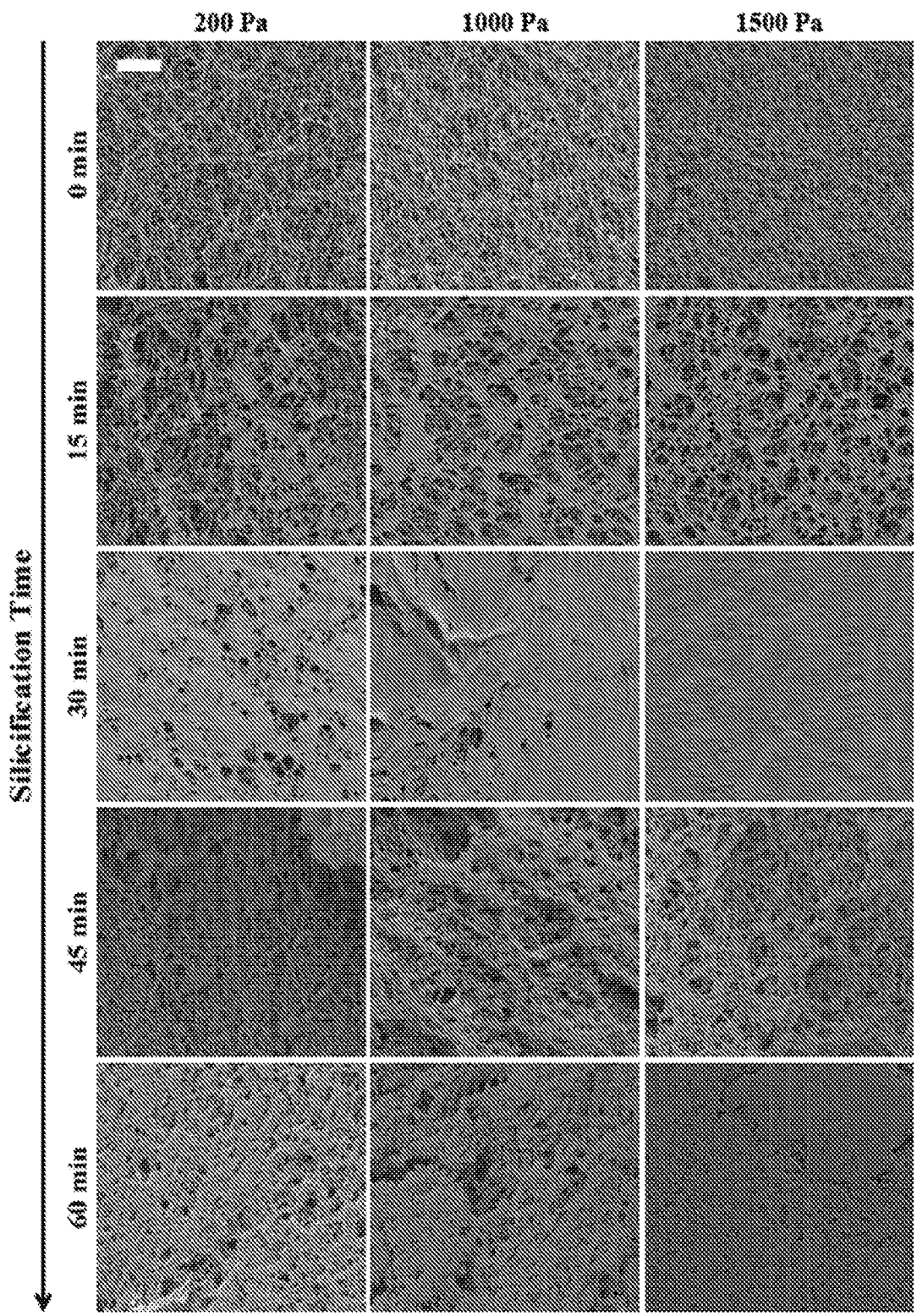
FIG. 5. A schematic cartoon illustrating two-phase polycondensation process.

To evaluate the combined effects of collagen fibril density and SS exposure time on hybrid material properties, collagen-fibril templates of varying fibril density, corresponding to G' values of 200, 1000, and 1500 Pa, were exposed to 3 vol % SS for 0-60 min. Referring now to FIG. 5, the development of the silica mineral layer is shown upon the collage-fibril template over time. Silica, which has previously been shown to nucleate upon individual collagen fibrils, appears to begin webbing together around 15 min to form a continuous initial layer around 30 min. The fibril density of the template determines the integrity of this initial layer, and the formation of a more complete, homogeneous coating at higher fibril densities can be attributed to their initiation of faster nucleation and gelation rates. After 30 min, a pure silica mineral layer continues to develop atop the initial hybrid layer at the template surface.

Mass transport properties were determined for collagen-fibril matrices with G' values of 200 and 1000 Pa that were infused with 4, 20, 40, or 150 kDa FITC-dextran and exposed to 3 vol % silicic acid for 0 or 30 min. The diffusion coefficient obtained for 150 kDa FITC-dextran was determined to be statistically different from any other diffusion coefficient by pairwise t-test ($p<0.05$) (data not shown). The lack of significance for silicification at the 200 Pa collagen level suggests that 1000 Pa collagen-fibril matrices, known to speed the rate of silica nucleation more than 200 Pa matrices, enable a minimum level of silicification required for effect to diffusivity. Based on images in FIG. 5, 15 min exposure to 3 vol % silicic acid is very unlikely to reach this minimum silicification requirement for any of the collagen-fibril templates investigated here due to the open, web-like structure of the hybrid interface. In a preferred embodiment, for applications requiring controlled diffusion across the tuned collagen-silica material, G' greater than 1000 Pa and silicic acid exposure longer than 30 min is used when using 3 vol % silicic acid.

The present disclosure demonstrates control over surface-localized silica condensation rates through interaction with collagen-fibril matrices that template and direct silica mineralization. Collagen-fibril templates that are tunable with respect to their microstructure and fibril density enable informed design of the absolute amount of synergistic charge-charge interactions between amine- and hydroxyl-containing collagen side chains with the ability to increase initiation rates of condensing silicic acid species (data not shown).

Figure 6:
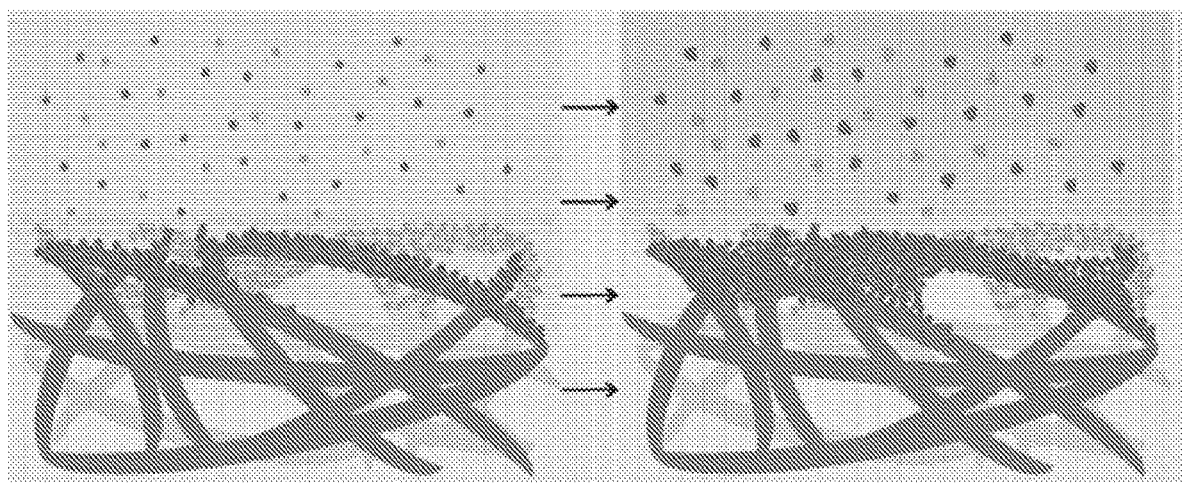
FIG. 6. SEM images (scale bar 10 µm) showing silicified surfaces for three different fibril densities (corresponding to G' of 200, 1000, and 1500 Pa) exposed to 3 vol % silicifying solution (SS) for five different times (0, 15, 30, 45, and 60 min).

FIG. 6 is a cartoon describing a two-phase process for silica mineralization of the collagen template. During Phase 1, collagen fibrils primarily contribute to localized gelation at the template surface by initiating condensation directly, while simultaneously increasing gelation rates in the bulk through more transient interactions with the surface. During Phase 2, collagen fibril surfaces become increasingly saturated with partially condensed silicate species, so preferential condensation initiation sites on the fibril surface become shielded from reactive silicic acid species. Additionally, the now silicified collagen fibril surface presents silicate groups to the surrounding solution, increasing the overall rate of bulk gelation as greater numbers of condensation events decrease $pK_a$ values for available hydroxyls attached to silicon atoms, resulting in deprotonation at the peak gelation condition of neutral pH. It is important to recognize that surface and bulk gelation occur simultaneously during both Phase 1 and Phase 2.

The key implication of such a two-phase process is that, for any TMOS-derived and collagen-templated silica mineralization process, the initial rate of Phase 1 surface condensation must exceed the rate of Phase 1 bulk condensation to form a continuous mineral layer at the organic template surface and facilitate removal of the bulk prior to complete gelation. Additionally, the rate of Phase 1 surface condensation relative to the rate of Phase 2 bulk condensation should determine the thickness and penetration of the mineral layer. For such diverse applications as cellular micro-encapsulation and biomimetic organic-inorganic materials, Phase 1 and Phase 2 kinetics are important experimental design factors to control.

Figure 7:
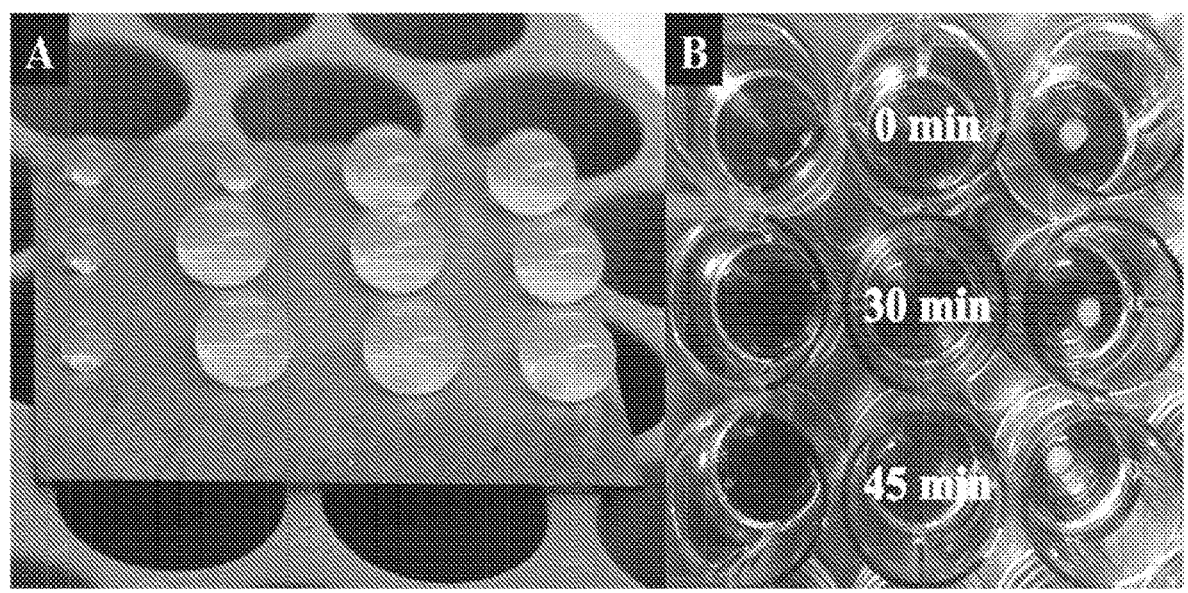
FIG. 7A. A photograph of 5 and 30 µL collagen-fibril microspheres showing their conformation prior to silicification.
FIG. 7B. A photograph of 5 and 30 µL collagen-fibril microspheres showing their conformation following silicification with 3 vol % SS ("silicified") for 30 and 45 min.
Figure 8:
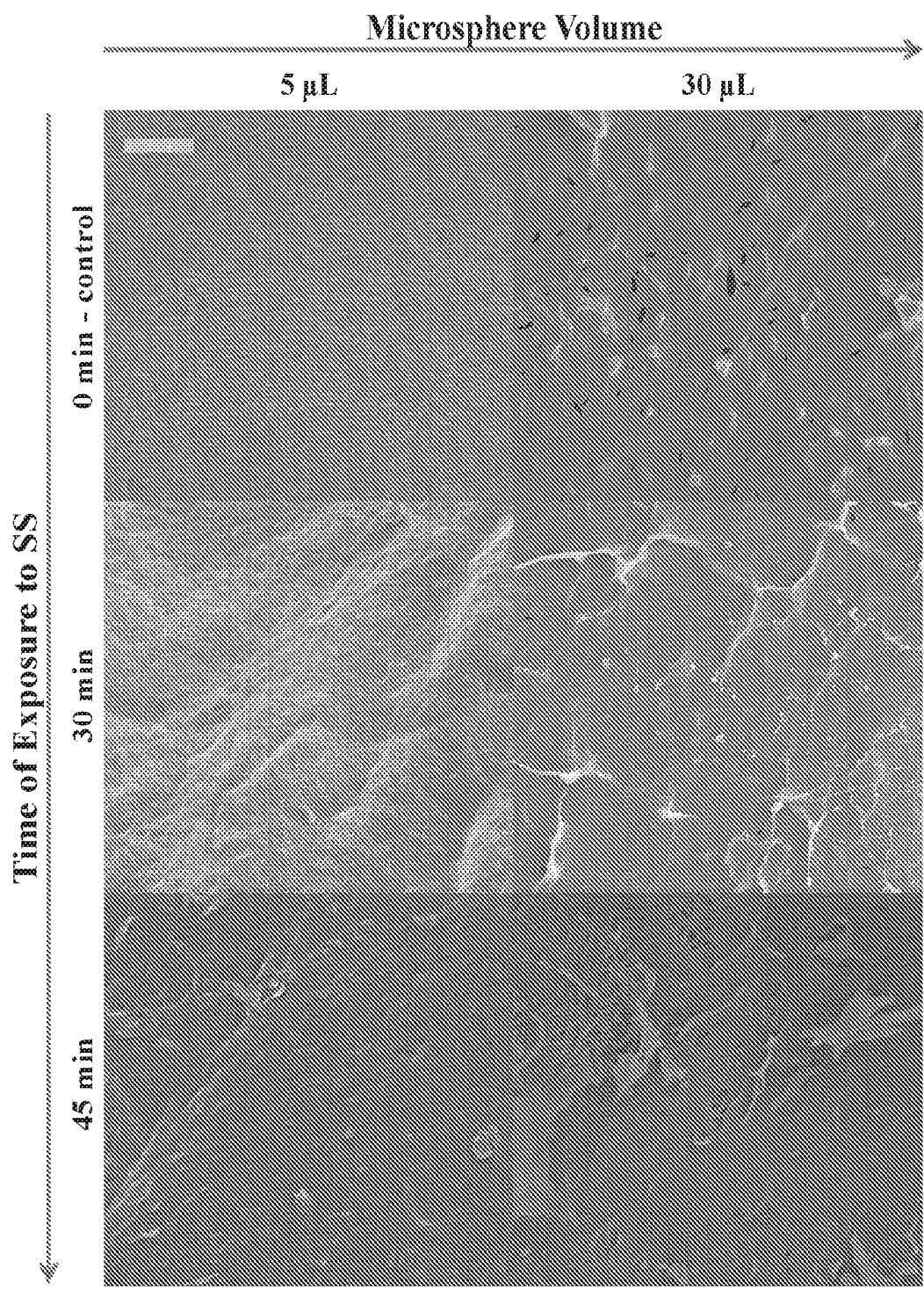
FIG. 8. SEM images (scale bar 5 µm) showing 5 and 30 µL collagen-fibril microspheres (1000 Pa) exposed to 3 vol % SS for 30 and 45 min.

Referring now to FIG. 7, collagen-fibril matrices were formed into microsphere conformations using a super hydrophobic surface. 5 and 30 µL microspheres of collagen (G'=1000 Pa) were created and exposed to 3 vol % SS for 0, 30, or 45 min. Photographs of microspheres before and after silicification are shown in FIG. 7A and FIG. 7B, respectively. Exposure times were chosen for their likelihood to produce thin yet porous layers, as determined by experimental sample images in FIG. 5. SEM images of the microsphere surfaces are shown in FIG. 8.

During storage and silicification, all collagen microspheres exhibited a minor amount of flattening but maintained their rounded conformation overall. Small sample volume, particularly for 5 µL microspheres, necessitated addition of a fixative (Tissue Tek™ O.C.T. compound) prior to sample drying. Despite minimal application to the sample underside, the fixative was taken up by samples, resulting in partially obscured microstructures for both sizes and completely collapsed macrostructures for smaller microspheres. Regardless, textured microstructure for exposure to SS is observed and developed more at 45 min than 30 min.

Figure 9:
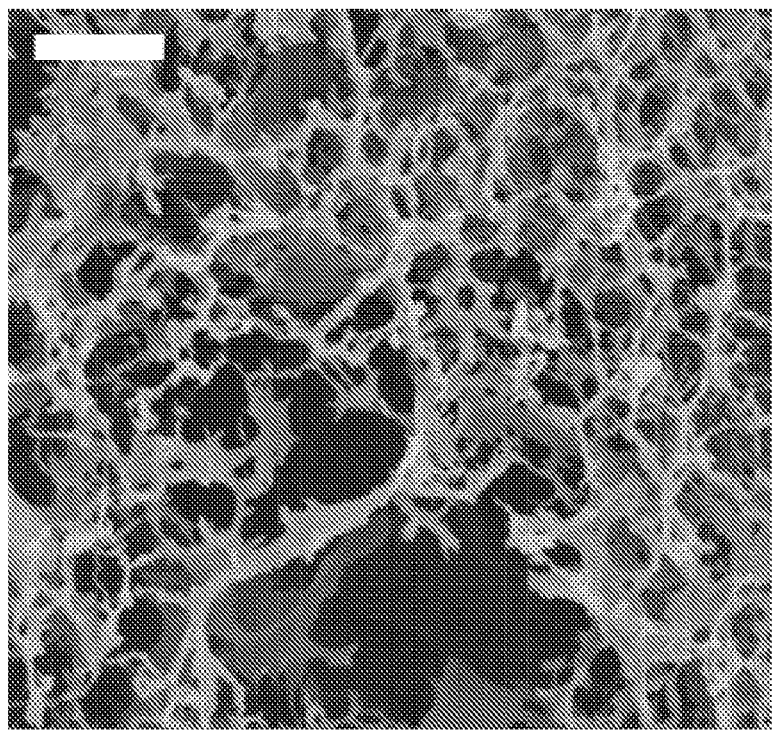
FIG. 9. SEM images (scale bar 5 µm) showing secondary silica layer formed at the surface of a 30 µL collagen-fibril microspheres (1000 Pa) exposed to 3 vol % SS for 45 min.

FIG. 9 shows a portion of the surface of a 30 µL microsphere that was exposed to SS for 45 min that was not obscured by preparation techniques, demonstrating development of the secondary silica layer atop the hybrid interface.

Figure 10:
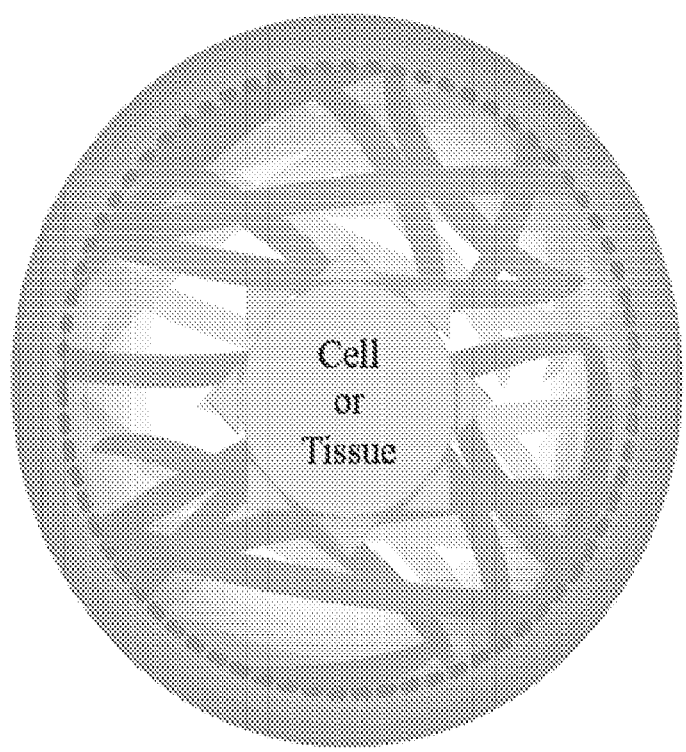
FIG. 10. A cartoon showing a cellular microencapsulation within collagen-silica hybrid materials.

FIG. 10 depicts a conceptualized design of cell or tissue encapsulation using collagen-templated sol-gel silica materials, where the cell is biologically supported by suspension within the collagen-fibril matrix but coated with a porous silica layer with improved mechanical strength and the potential for biochemical protection by size exclusion.

Experimental Section

Preparation of Collagen-Fibril Matrices:

Type I collagen oligomers were acid solubilized from the dermis of market weight pigs and lyophilized for storage as described previously. Prior to use, lyophilized oligomer was dissolved in 0.01 N hydrochloric acid (HCl) and rendered aseptic by chloroform exposure at 4° C. Oligomer concentration was determined using a Sirius Red (Direct Red 80) assay. The oligomer formulation was standardized based on molecular composition as well as polymerization capacity according to ASTM standard F3089-14. Here, polymerization capacity is defined by matrix shear storage modulus G' as a function of oligomer concentration of the polymerization reaction. Collagen-fibril matrices of four different fibril densities (corresponding to shear storage modulus G' values of 200 Pa, 600 Pa, 1000 Pa, and 1500 Pa) were prepared by dilution in 0.01 N HCl and neutralization with 10× phosphate-buffered saline (PBS, 1×PBS had 0.17 M total ionic strength and pH 7.4) and 0.1 N sodium hydroxide (NaOH) to achieve neutral pH (7.4). Neutralized collagen solutions were kept on ice prior to induction of polymerization at 37° C. Individual collagen-fibril matrices were drop cast and polymerized in 500 µL volumes in 24-well plates for rheological analysis and in 58 µL volumes in 96-well plates for all other analyses.

Preparation of Silicifying Solution (SS):

To produce concentrated silicic acid, tetramethoxysilane (tetramethyl orthosilicate, TMOS) (Sigma, USA) was hydrolyzed under acidic conditions in nanopure water adjusted to approximately pH 3 with HCl. Acidified water was added to TMOS such that the molar ratio of components (water:TMOS:HCl) was 16:1:0.007. The mixture was vortexed for 5-10 minutes. Methanol byproduct of TMOS hydrolysis was removed under vacuum by rotary evaporation at 46° C. to reduce the total volume by 40%, forming a concentrated (approximately 3.84 M) solution of silicic acids. The silicic acid solution was placed on ice and used immediately for individual experiments in either 3 vol % (approximately 115 mM) or 6 vol % (approximately 230 mM) concentrated silicic acid in 1×PBS, referred to as silicifying solution (SS).

Collagen-fibril matrices with G' values 200, 1000, and 1500 Pa were exposed to varied concentrations of SS (3 or 6 vol %) for varied times (0, 15, 30, 45, or 60 min) by submersion. Following exposure, matrices were washed thrice with 1×PBS to halt silicification. For surface analyses, silicified matrices were prepared for SEM and energy-dispersive x-ray spectroscopy (EDX) by ethanol dehydration (10%, 20%, 30%, 40%, 80%, 90%, 100% in water), liquid $CO_2$ exchange using a critical point dryer (LADD Research Industries, Williston, VT, USA), and sputter coating with platinum. For silica penetration depth studies, silicified matrices were flash-frozen in liquid nitrogen, cross-sectioned while frozen, and freeze-dried for 5 hours at −85° C. and $2.7 \times 10^{-3}$ Pa. Cross-sectioned samples were then mounted, sputter coated with platinum, and imaged by SEM.

3D collagen-fibril matrices of three different fibrillar densities (corresponding to quality controlled stiffness values of 200 Pa, 1000 Pa, and 1600 Pa) were prepared as described by Kreger, et al., see S. T. Kreger, B. J. Bell, J. Bailey, E. Stites, J. Kuske, B. Waisner, and S. L. Voytik-Harbin, *Biopolymers*, 93, 690-707 (2010). Briefly, lyophilized type I oligomeric collagen, derived from the dermis of market weight pigs, was dissolved and diluted in 0.01 N HCl and neutralized with 10× phosphate-buffered saline (PBS, 1×PBS had 0.17 M total ionic strength and pH 7.4) and 0.1 N NaOH to achieve neutral pH (7.4). Neutralized collagen solutions were kept on ice prior to induction of polymerization at 37° C. Individual collagen-fibril matrices were drop cast and polymerized in 250 µL volumes in 48-well plates for rheological analysis and in 58 µL volumes in 96-well plates for all other analyses.

Scanning Electron Microscopy (SEM):

Collagen-fibril matrices were exposed to silicifying solutions, SS, ("silicified") of varying concentrations (3, 6 vol % concentrated silicic acid in 1×PBS) for varying lengths of time (0, 15, 30, 45, 60 min). Following exposure, matrices were washed thrice with 1×PBS to halt silicification. Silicified collagen-fibril matrices were prepared for SEM and EDX by ethanol dehydration (10%, 20%, 30%, 40%, 80%, 90%, 100% in water), liquid $CO_2$ exchange using a critical point dryer (LADD Research Industries, Williston, VT, USA), and sputter coating with platinum.

High-resolution SEM images were obtained in high vacuum mode with an acceleration voltage of 5 kV using the NOVA nanoSEM FESEM (FEI Company, Hillsboro, OR, USA). equipped with Everhart Thornley Detector (ETD) and Through-the-Lens Detector (TLD). Energy-dispersive X-ray Spectroscopy (EDX) measurements were obtained in high vacuum mode with an acceleration voltage of 5 kV using the Quanta 3D FEG Dual-Beam SEM (FEI Company) equipped with EDX detector.

Rheological characteristics of prepared collagen-silica samples were determined using a rotational AR-G2 rheometer with SMART SWAP™ geometry (TA Instruments, USA). A parallel plate upper geometry (8 mm diameter) was attached, and collagen samples were placed between the mobile upper plate and the stationary lower plate with a gap distance of 350 µm. Viscoelastic properties were measured at a constant frequency (1 Hz, 6.283 rad/s) over the strain range of 0.01-5% at 37° C.

Cell viability can be tested with commercial live/dead assays based on determination of cell membrane integrity and metabolic activity using fluorescence quantification and confocal microscopy. Cell identity and hormone production will be examined by immunohistochemical staining and imaging for insulin, glucagon, and somatostatin. Beta cell associated gene transcripts (pdx1, insulin, pre-insulin) can be examined by RT-PCR. Islet function will be assessed by glucose stimulated insulin (GSIS) release assay, which uses ELISA to measure released insulin at high and low levels of glucose. For all assays we can compare the three conditions (control, +silica, +silica/collagen) at 1, 4 and 7 days after treatment. All methods will be conducted as previously described. See U.S. Patent Publication No. 2012/0178137, disclosures of which are incorporated by reference in its entirety to the extent they are not inconsistent with the explicit teachings of this specification.

In another embodiment, the kit comprises a solution comprising isolated collagen, a phosphate buffer solution, a glucose solution, a calcium chloride solution, an acid solution, and a basic neutralizing solution. In another embodiment, the kit can include at least one isolated collagen monomer, a silicifying solution, and a polymerization buffer. In one embodiment the polymerization composition comprises a phosphate buffer that has a pH of about 7.2 to about 7.6 and the acid solution is an acetic acid solution comprising about 0.05N to about 0.005N acetic acid. In another embodiment, the acid solution is about 0.01N acetic acid. In another embodiment the polymerization composition comprises a phosphate buffer that has a pH of about 7.2 to about 7.6 and the acid solution is a hydrochloric acid solution comprising about 0.05N to about 0.005N hydrochloric acid. In another embodiment, the acid solution is about 0.01N hydrochloric acid. In one embodiment, the glucose solution has a concentration selected from the range of about 0.2% to about 5% w/v glucose, or about 0.5% to about 3% w/v glucose, and in one embodiment the glucose solution is about 1% w/v glucose. In one embodiment the $CaCl_2$ solution has a concentration selected from the range of about 2 mM to about 40.0 mM $CaCl_2$ or about 0.2 mM to about 4.0 mM $CaCl_2$, or about 0.2 to about 2 mM $CaCl_2$. In one embodiment the kit is provided with a 10×PBS buffer having a pH of about pH 7.4, and comprising about 1.37M NaCl about 0.027M KCl, about 0.081M $Na_2HPO_4$, about 0.015M $KH_2PO_4$, about 5 mM $MgCl_2$ and about 1% w/v glucose. In another embodiment, kits are provided that comprise three-dimensional, preformed silicified tuned collagen materials prepared according to any of the methods described herein and wherein the kits comprise any of the components described herein.

The kits can further comprise instructional materials describing methods for mixing the kit reagents to prepare tuned or engineered matrices or describing methods for using preformed, three-dimensional silicified tuned collagen materials. In particular, the instructional materials can provide information regarding the final concentrations that give optimal microenvironmental conditions including fibril microstructure and mechanical properties for a particular cell type or for a particular desired result.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed:

1. A composition comprising:
   a crosslinked polymerized oligomeric collagen network wherein the crosslinks consist of natural intermolecular crosslinks, and
   a porous condensed silica layer formed on the polymerized oligomeric collagen only at the surface of the outermost layer of the collagen network.

2. The composition of claim 1, further comprising at least one biological material.

3. The composition of claim 2, wherein the at least one biological material is selected from the group consisting of bio-elements, biomolecules, biogenic substances, biotic materials, natural materials, bio-based materials, biocompatible materials, bio-composites, biomasses, bodily fluids, cellular components, organic matters, cytokines, and tissues.

4. The composition of claim 2, wherein the at least one biological material is selected from the group consisting of bacterial cell, plant cell, fungal cell, somatic cell, stem cell, pluripotent stem cell, induced pluripotent stem cell, multipotent stem cell, totipotent stem cell, genetically engineered cell, pancreatic cell, beta cell, isolated islet cell, tissue, nutrient, enzyme, protein, cytokine, vasodilator, and vasoconstrictor.

5. The composition of claim 2, wherein the at least one biological material is human in origin.

6. A method for making a composition of claim 1, comprising the steps of:
   creating a polymerized oligomeric collagen having a first surface and a second surface;
   exposing said polymerized oligomeric collagen to a silicifying solution to form a silicified polymerized oligomeric collagen; and
   washing said polymerized oligomeric collagen with at least one buffer which stops the silicifying process.

7. The method according to claim 6, wherein the polymerized oligomeric collagen is created by polymerizing an isolated polymerizable oligomeric collagen.

8. The method of claim 6, wherein the silicifying solution is formed by: hydrolyzing tetramethoxysilane under acidic conditions in water; and removing most, if not all, of the methanol by-product.

9. The method of claim 6, wherein said exposing step is a two-phase process including a Phase 1 surface condensation step and a Phase 2 bulk condensation step, wherein the initial rate of the Phase 1 surface condensation exceeds the rate of the Phase 2 bulk condensation step to form a continuous silica layer on the first surface of the polymerized oligomeric collagen.

10. The method of claim 6, further including contacting the second surface of the polymerized oligomeric collagen with at least one biological material selected from the group consisting of: bacterial cell, plant cell, fungal cell, somatic cell, stem cell, pluripotent stem cell, induced pluripotent stem cell, multipotent stem cell, totipotent stem cell, genetically engineered cell, pancreatic cell, beta cell, isolated islet cell, tissue, nutrient, enzyme, protein, cytokine, vasodilator, and vasoconstrictor.

11. The composition of claim 1, wherein the composition is a sphere, wherein the sphere includes at least one pore and the pore can selectively diffuse biomolecules.

12. The composition of claim 2, wherein the composition is a sphere.

13. The composition of claim 12, wherein the sphere includes at least one pore and the pore can selectively diffuse biomolecules.

14. The composition of claim 1, wherein the polymerized oligomeric collagen is in the form of a three-dimensional fibrillar matrix.

15. The composition of claim 14, further comprising at least one biological material.

16. The composition of claim 15, wherein the at least one biological material is selected from the group consisting of bio-elements, biomolecules, biogenic substances, biotic materials, natural materials, bio-based materials, biocompatible materials, bio-composites, biomasses, bodily fluids, cellular components, organic matters, cytokines, and tissues.

17. The composition of claim 15, wherein the at least one biological material is selected from the group consisting of bacterial cell, plant cell, fungal cell, somatic cell, stem cell, pluripotent stem cell, induced pluripotent stem cell, multipotent stem cell, totipotent stem cell, genetically engineered cell, pancreatic cell, beta cell, isolated islet cell, tissue, nutrient, enzyme, protein, cytokine, vasodilator, and vasoconstrictor.

18. The composition of claim 14, wherein the composition is a sphere.

19. The composition of claim 18, wherein the sphere includes at least one pore and the pore can selectively diffuse biomolecules.

20. The composition of claim 15, wherein the polymerized oligomeric collagen's three-dimensional fibrillar matrix at least partially encapsulates the at least one biological material.

21. The composition of claim 16, wherein the polymerized oligomeric collagen's three-dimensional fibrillary matrix at least partially encapsulates the at least one biological material.

22. The composition of claim 17, wherein the polymerized oligomeric collagen's three-dimensional fibrillar matrix at least partially encapsulates the at least one biological material.

23. The composition of claim 15, wherein the at least one biological material is suspended in the polymerized oligomeric collagen's three-dimensional fibrillar matrix.

24. The composition of claim 16, wherein the at least one biological material is suspended in the polymerized oligomeric collagen's three-dimensional fibrillar matrix.

25. The composition of claim 17, wherein the at least one biological material is suspended in the polymerized oligomeric collagen's three-dimensional fibrillar matrix.

26. The composition of claim 1, wherein the crosslinks are covalent crosslinks, and the pores of said condensed silica layer have a size selected from a range of about 50 nm to about 750 nm.

27. The composition of claim 1, wherein the crosslinks are selected from aldol, hydroxyaldol, and ketoimine linkages.

28. The composition of claim 27, wherein the crosslinks are enzymatically catalyzed linkages.

* * * * *